(12) United States Patent
DeVita et al.

(10) Patent No.: US 7,704,988 B2
(45) Date of Patent: Apr. 27, 2010

(54) ANTI-HYPERCHOLESTEROLEMIC COMPOUNDS

(75) Inventors: Robert J. DeVita, Westfield, NJ (US); Gregori J. Morriello, Randolph, NJ (US); Peter Lin, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 828 days.

(21) Appl. No.: 11/542,966

(22) Filed: Oct. 4, 2006

(65) Prior Publication Data

US 2007/0078098 A1  Apr. 5, 2007

Related U.S. Application Data

(60) Provisional application No. 60/723,781, filed on Oct. 5, 2005.

(51) Int. Cl.
| | | |
|---|---|---|
| *C07D 205/08* | (2006.01) | |
| *A61K 31/397* | (2006.01) | |
| *A61P 9/10* | (2006.01) | |
| *A61P 3/06* | (2006.01) | |
| *C07H 7/02* | (2006.01) | |
| *A61K 31/7052* | (2006.01) | |

(52) U.S. Cl. ............... 514/210.02; 540/200; 514/32; 536/17.4; 564/58; 564/90; 564/98; 549/372

(58) Field of Classification Search ............ 540/200; 514/210.02
See application file for complete search history.

(56) References Cited

U.S. PATENT DOCUMENTS

| | | | |
|---|---|---|---|
| 5,846,966 A | 12/1998 | Rosenblum et al. | |
| RE37,721 E | 5/2002 | Rosenblum et al. | |
| 7,045,515 B2 | 5/2006 | Tomiyama et al. | |
| 7,388,004 B2* | 6/2008 | Jaehne et al. | 514/210.02 |
| 7,390,790 B2* | 6/2008 | Jaehne et al. | 514/23 |
| 2002/0137689 A1 | 9/2002 | Glombik et al. | |
| 2004/0198700 A1* | 10/2004 | Burnett et al. | 514/210.02 |
| 2005/0267049 A1* | 12/2005 | Goulet et al. | 514/210.02 |
| 2007/0078098 A1* | 4/2007 | DeVita et al. | 514/210.02 |
| 2008/0274947 A1* | 11/2008 | Jaehne et al. | 514/210.02 |
| 2009/0005321 A1* | 1/2009 | Zimmer et al. | 514/210.02 |
| 2009/0137546 A1* | 5/2009 | DeVita et al. | 514/210.02 |
| 2009/0264402 A1* | 10/2009 | Jaehne et al. | 514/210.02 |

FOREIGN PATENT DOCUMENTS

WO  WO2006/138163 A2  12/2006

OTHER PUBLICATIONS

JAMA, "Executive Summary of the Third Report of the National Cholesterol Education Program (NCEP) Expert Panel on Detection, Evaluation, and Treatment of High Blood Cholesterol in Adults (Adult Treatment Panel III)", 285:2486-2497, 2001.
Burnett et al., "Synthesis of Iodinated Biochemical Tools Related to the 2-Azetidinone Class of Cholesterol Absorption Inhibitors", Bioorganic and Medical Chemistry Letters, 12:311-314, 2002.

* cited by examiner

*Primary Examiner*—Mark L Berch
(74) *Attorney, Agent, or Firm*—Dianne Pecorero; Mark R. Daniel; Carol S. Quagliato

(57) ABSTRACT

This invention provides cholesterol absorption inhibitors of Formula I:

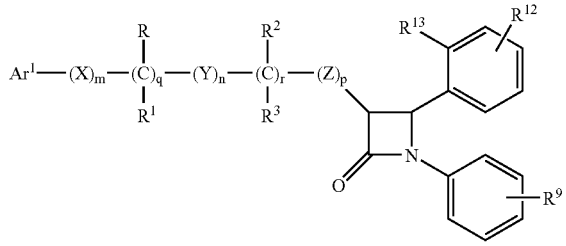

and the pharmaceutically acceptable salts and esters thereof. The compounds are useful for lowering plasma cholesterol levels, particularly LDL cholesterol, and for treating and preventing atherosclerosis and atherosclerotic disease events.

20 Claims, No Drawings

ANTI-HYPERCHOLESTEROLEMIC COMPOUNDS

CROSS REFERENCE TO RELATED APPLICATION

This application claims the benefit of U.S. Provisional Application No. 60/723,781, filed Oct. 5, 2005, under 35 U.S.C. 119(e).

BACKGROUND OF THE INVENTION

The instant invention relates to substituted 2-azetidinones and the pharmaceutically acceptable salts and esters there of, and to their use alone or in combination with other active agents to treat hypercholesterolemia and for preventing, halting or slowing the progression of atherosclerosis and related conditions and disease events.

It has been clear for several decades that elevated blood cholesterol is a major risk factor for coronary heart disease, and many studies have shown that the risk of CHD events can be reduced by lipid-lowering therapy. Prior to 1987, the lipid-lowering armamentarium was limited essentially to a low saturated fat and cholesterol diet, the bile acid sequestrants (cholestyramine and colestipol), nicotinic acid (niacin), the fibrates and probucol. Unfortunately, all of these treatments have limited efficacy or tolerability, or both. Substantial reductions in LDL (low density lipoprotein) cholesterol accompanied by increases in HDL (high density lipoprotein) cholesterol could be achieved by the combination of a lipid-lowering diet and a bile acid sequestrant, with or without the addition of nicotinic acid. However, this therapy is not easy to administer or tolerate and was therefore often unsuccessful except in specialist lipid clinics. The fibrates produce a moderate reduction in LDL cholesterol accompanied by increased HDL cholesterol and a substantial reduction in triglycerides, and because they are well tolerated these drugs have been more widely used. Probucol produces only a small reduction in LDL cholesterol and also reduces HDL cholesterol, which, because of the strong inverse relationship between HDL cholesterol level and CHD risk, is generally considered undesirable. With the introduction of lovastatin, the first inhibitor of HMG-CoA reductase to become available for prescription in 1987, for the first time physicians were able to obtain large reductions in plasma cholesterol with very few adverse effects.

Recent studies have unequivocally demonstrated that lovastatin, simvastatin and pravastatin, all members of the HMG-CoA reductase inhibitor class, slow the progression of atherosclerotic lesions in the coronary and carotid arteries. Simvastatin and pravastatin have also been shown to reduce the risk of coronary heart disease events, and in the case of simvastatin a highly significant reduction in the risk of coronary death and total mortality has been shown by the Scandinavian Simvastatin Survival Study. This study also provided some evidence for a reduction in cerebrovascular events. Despite the substantial reduction in the risk of coronary morbidity and mortality achieved by simvastatin, the risk is still substantial in the treated patients. For example, in the Scandinavian Simvastatin Survival Study, the 42% reduction in the risk of coronary death still left 5% of the treated patients to die of their disease over the course of this 5 year study. Further reduction of risk is clearly needed.

A more recent class of anti-hyperlipidemic agents that has emerged includes inhibitors of cholesterol absorption. Ezetimibe, the first compound to receive regulatory approval in this class, is currently marketed in the U.S. under the tradename ZETIA®. Ezetimibe has the following chemical structure and is described in U.S. Pat. Nos. Re. 37,721 and 5,846,966:

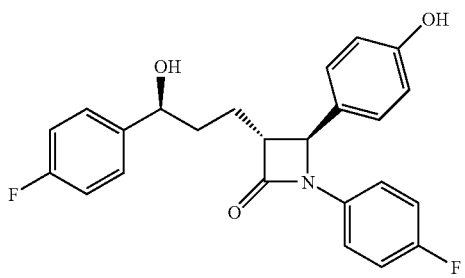

Sugar-substituted 2-azetidinones, including glucuronidated analogs of the following general structure:

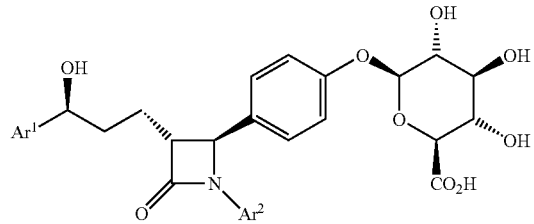

and methods for making them are disclosed in U.S. Pat. No. 5,756,470, wherein $Ar^1$ and $Ar^2$ are unsubstituted or substituted aryl groups.

Additional cholesterol absorption inhibitors are described in WO2002/066464 A1 (applied for by Kotobuki Pharmaceutical Co.), and US2002/0137689 A1 (Glombik et al.). WO2002/066464 A1 discloses hypolipidemic compounds of general formula

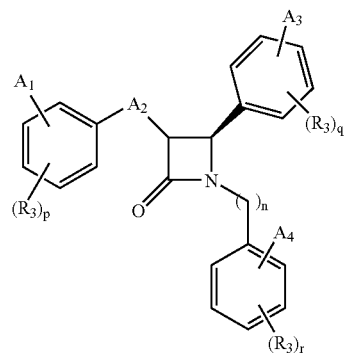

wherein, among other definitions, $A_1$, $A_3$ and $A_4$ can be

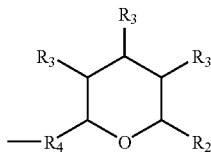

and wherein $R_2$ is —$CH_2OH$, —$CH_2OC(O)$—$R_1$, or —$CO_2R_1$; $R_3$ is —OH or —OC(O)$R_1$, and $R_4$ is —$CH_2)_kR_5$ $(CH_2)_i$— where k and i are zero or integers of one or more, and k+i is an integer of 10 or less; and $R_5$ is a single bond, —CH=CH—, —$OCH_2$—, carbonyl or —CH(OH).

US2002/0137689 A1 discloses hypolipidemic compounds of general formula

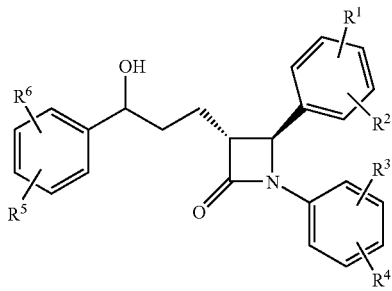

wherein, among other definitions, $R^1$, $R^2$, $R^3$, $R^4$, $R^5$, $R^6$ independently of one another can be $(C_0-C_{30})$-alkylene-(LAG), where one or more carbon atoms of the alkylene radical may be replaced by —O—, —(C=O)—, —CH=CH—, —C≡C—, —N(($C_1$-$C_6$)-alkyl)-, —N(($C_1$-$C_6$)-alkylphenyl) or —NH—; and (LAG) is a sugar residue, disugar residue, trisugar residue, tetrasugar residue; a sugar acid, or an amino sugar.

In the ongoing effort to discover novel treatments for hyperlipidemia and atherosclerotic process, the instant invention provides novel cholesterol absorption inhibitors, described below.

SUMMARY OF THE INVENTION

One object of the instant invention is to provide novel cholesterol absorption inhibitors of Formula I

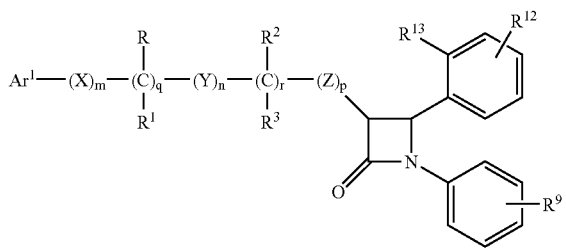

and the pharmaceutically acceptable salts and esters thereof.

A second object of the instant invention is to provide a method for inhibiting cholesterol absorption comprising administering a therapeutically effective amount of a compound of Formula I to a patient in need of such treatment. Another object is to provide a method for reducing plasma cholesterol levels, especially LDL-cholesterol, and treating hypercholesterolemia comprising administering a therapeutically effective amount of a compound of Formula I to a patient in need of such treatment.

As a further object, methods are provided for preventing or reducing the risk of developing atherosclerosis, as well as for halting or slowing the progression of atherosclerotic disease once it has become clinically evident, comprising the administration of a prophylactically or therapeutically effective amount, as appropriate, of a compound of Formula I to a patient who is at risk of developing atherosclerosis or who already has atherosclerotic disease. Another object of the present invention is the use of the compounds of the present invention for the manufacture of a medicament useful in treating, preventing or reducing the risk of developing these conditions. Other objects of this invention are to provide processes for making the compounds of Formula I and to provide novel pharmaceutical compositions comprising these compounds.

Additionally the compounds of this invention, particularly radioactive isotopes of the compounds of Formula I, can be used in screening assays, where the assay is designed to identify new cholesterol absorption inhibitors that have the same mechanism of action as ezetimibe. Additional objects will be evident from the following detailed description.

DETAILED DESCRIPTION OF THE INVENTION

The novel cholesterol absorption inhibitors of the instant invention are compounds of structural Formula I

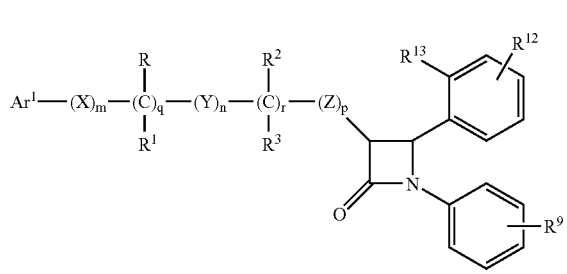

and the pharmaceutically acceptable salts and esters thereof, wherein $Ar^1$ is selected from the group consisting of aryl and $R^4$-substituted aryl;

X, Y and Z are independently selected from the group consisting of —$CH_2$—, —CH($C_{1-6}$alkyl)— and —C($C_{1-6}$alkyl)$_2$—;

R is selected from the group consisting of —$OR^6$, —O(CO)$R^6$, —O(CO)O $R^8$, —O(CO)$NR^6R^7$, a sugar residue, a disugar residue, a trisugar residue and a tetrasugar residue;

$R^1$ is selected from the group consisting of —H, —$C_{1-6}$alkyl and aryl, or R and $R^1$ together are oxo;

$R^2$ is selected from the group consisting of —$OR^6$, —O(CO)$R^6$, —O(CO)$OR^8$ and —O(CO)$NR^6 R^7$;

$R^3$ is selected from the group consisting of —H, —$C_{1-6}$alkyl and aryl, or $R^2$ and $R^3$ together are oxo;

q and r are integers each independently selected from 0 and 1 provided that at least one of q and r is 1;

m, n and p are integers each independently selected from 0, 1, 2, 3 and 4, provided that the sum of m, n, p, q and r is 1, 2, 3, 4, 5 or 6;

t is an integer selected from 0, 1 and 2;

$R^4$ is 1-5 substituents independently selected at each occurrence from the group consisting of: —$OR^5$, —O(CO)$R^5$, —O(CO)$OR^8$, —O—$C_{1-5}$alkyl-$OR^5$, —O(CO)$NR^5R^6$, —$NR^5R^6$, —$NR^5$(CO)$R^6$, —$NR^5$(CO)$OR^8$, —$NR^5$(CO)$NR^6R^7$, —$NR^5SO_2R^8$, —$COOR^5$, —$CONR^5R^6$, —$COR^5$, —$SO_2NR^5R^6$, —S(O)$_tR^8$, —O—$C_{1-10}$alkyl-$COOR^5$, —O—$C_{1-10}$alkyl-$CONR^5R^6$ and fluoro;

$R^5$, $R^6$ and $R^7$ are independently selected at each occurrence from the group consisting of —H, —$C_{1-6}$alkyl, aryl and aryl-substituted —$C_{1-6}$alkyl;

$R^8$ is selected from the group consisting of —$C_{1-6}$alkyl, aryl and aryl-substituted —$C_{1-6}$alkyl;

$R^9$ is selected from the group consisting of —C≡C—$(CH_2)_y$—$NR^{10}R^{11}$, —C=C—$(CH_2)_y$$NR^{10}R^{11}$ and —$(CH_2)_w$—$NR^{10}R^{11}$;

w is an integer selected from 1, 2, 3, 4, 5, 6, 7 and 8; and y is an integer selected from 1, 2, 3, 4, 5 and 6; and $R^{10}$ is selected from the group consisting of —H and —$C_{1-3}$alkyl;

$R^{11}$ is selected from the group consisting of —H, —$C_{1-3}$alkyl, —C(O)—$C_{1-3}$alkyl, —C(O)—$NR^{10}R^{10}$, —$SO_2$—$C_{1-3}$alkyl, and —$SO_2$-phenyl;

$R^{12}$ is selected from the group consisting of —$C_{1-15}$alkyl mono- or poly-substituted with —OH, —CH=CH—$C_{1-13}$alkyl mono- or poly-substituted with —OH, —C≡C—$C_{1-13}$alkyl mono- or poly-substituted with —OH, and

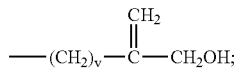

v is an integer selected from 0 and 1; and $R^{13}$ is selected from the group consisting of —H and —OH.

In one embodiment of this invention are compounds of Formula I wherein the sum of m, q and n is 1, 2, 3, 4, or 5 when p is 0 and r is 1.

In another embodiment of this invention are compounds of Formula I wherein r is zero and m is zero.

In a another embodiment of this invention are compounds Formula I having structural Formula Ia,

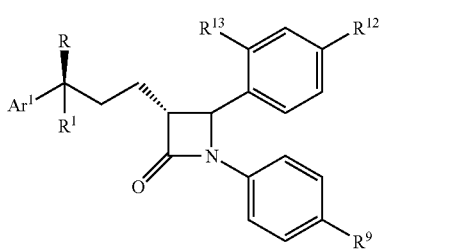

and the pharmaceutically acceptable salts and esters thereof, wherein the variables ($Ar^1$; R, $R^1$, $R^9$, $R^{12}$, $R^{13}$) are as defined in Formula I.

In another embodiment of this invention are compounds Formula I having structural Formula Ib,

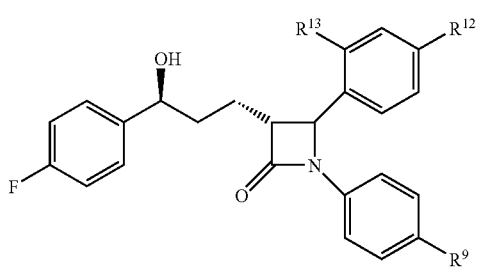

and the pharmaceutically acceptable salts and esters thereof, wherein the variables ($R^9$, $R^{12}$, $R^{13}$) are as defined in Formula I.

In another embodiment of this invention are compounds of Formula I and Ia wherein $Ar^1$ is selected from the group consisting of aryl and $R^4$-substituted aryl wherein $R^4$ is 1-2 substituents independently selected at each occurrence from the group consisting of: —$OR^5$, —O(CO)$R^5$, —O(CO)$OR^8$, —O—$C_{1-5}$alkyl-$OR^5$, —O(CO)$NR^5R^6$, —$NR^5R^6$, —$NR^5$(CO)$R^6$, —$NR^5$(CO)$OR^8$, —$NR^5$(CO)$NR^6R^7$, —$NR^5SO_2R^8$, —$COOR^5$, —$CONR^5R^6$, —$COR^5$, —$SO_2NR^5R^6$, —S(O)$_rR^8$, —O—$C_{1-10}$alkyl-$COOR^5$, —O—$C_{1-10}$alkyl-$CONR^5R^6$ and fluoro. In a class of this embodiment, $Ar^1$ is unsubstituted, mono- or di-substituted phenyl. In a sub-class, $Ar^1$ is phenyl mono-substituted with fluoro, and particularly 4-fluoro-phenyl.

In another embodiment of this invention are compounds of Formula I and Ia wherein R is —$OR^6$; in a class of this embodiment, R is —OH.

In another embodiment of this invention are compounds of Formula I and Ia wherein $R^1$ is —H.

In another embodiment of this invention are compounds of Formula I and Ia wherein $R^2$ is —$OR^6$; in a class of this embodiment, $R^2$ is —OH.

In another embodiment of this invention are compounds of Formula I and Ia wherein $R^3$ is —H.

In another embodiment of this invention are compounds of Formula I, Ia and Ib wherein $R^9$ is —$(CH_2)_w$—$NR^{10}R_{11}$. In a class of this embodiment, $R^{11}$ is selected from —$SO_2$—$C_{1-3}$alkyl and —$SO_2$-phenyl. In a sub-class of this class, $R^9$ is —$(CH_2)_w NR^{10}$—$SO_2CH_3$. In a further sub-class, w is an integer selected from 3, 4, 5 and 6.

In another embodiment of this invention are compounds of Formula I, Ia and Ib wherein $R^9$ is —C≡C—$(CH_2)_y$—$NR^{10}R^{11}$. In a class of this embodiment, $R^{11}$ is selected from —$SO_2$—$C_{1-3}$alkyl and —$SO_2$-phenyl. In a sub-class of this class, $R^9$ is —C≡C—$(CH_2)_y$—$NR^{10}$—$SO_2CH_3$. In a further sub-class, y is an integer selected from 1, 2, 3 and 4.

In another embodiment of this invention are compounds of Formula I, Ia and Ib wherein $R^9$ is —C≡C—$(CH_2)_y$—$NR^{10}R^{11}$. In a class of this embodiment, $R^{11}$ is selected from —$SO_2$—$C_{1-3}$alkyl and —$SO_2$-phenyl. In a sub-class of this class, $R^9$ is —C≡C—$(CH_2)_y$—$NR^{10}$—$SO_2CH_3$. In a further sub-class, y is an integer selected from 1, 2, 3 and 4.

In another embodiment of this invention are compounds of Formula I and Ia wherein $R^{10}$ is selected from —H and methyl.

In another embodiment of this invention are compounds of Formula I and Ia wherein $R^{11}$ is selected from —$SO_2$—$C_{1-3}$alkyl and —$SO_2$-phenyl.

In another embodiment of this invention are compounds of Formula I, Ia and Ib wherein —$C_{1-15}$alkyl mono- or poly-substituted with —OH. In a class of this embodiment, $R^{12}$ is —$C_{1-8}$alkyl mono- or poly-substituted with —OH. In a sub-class of this class, $R^{12}$ is —$C_{3-6}$ alkyl mono- or poly-substituted with —OH.

In another embodiment of this invention are compounds of Formula I, Ia and Ib wherein $R^{12}$ is —CH=CH—$C_{1-13}$alkyl mono- or poly-substituted with —OH.

In another embodiment of this invention are compounds of Formula I, Ia and Ib wherein $R^{12}$ is —C≡C—$C_{1-13}$alkyl mono- or poly-substituted with —OH.

In another embodiment of this invention are compounds of Formula I, Ia and Ib wherein $R^{12}$ is

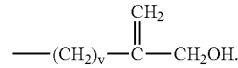

Each embodiment, class or sub-class described above for each variable (i.e., $Ar^1$, R, $R^1$, $R^9$, $R^{12}$, etc.) in Formulas I, Ia and Ib may be combined with one or more of the embodiments, classes or sub-classes described above for one or more other variables, and all such sub-generic combinations are included within the scope of this invention.

As used herein "alkyl" is intended to include both branched- and straight-chain saturated aliphatic hydrocarbon groups having the specified number of carbon atoms. Examples of alkyl groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), secbutyl (s-Bu), tertbutyl (t-Bu), 1-methylpropyl, 2-methylbutyl, 3-methylbutyl, isopentyl, isohexyl and the like. If there is no specified prefix (such as "n-" for normal, "s-" for sec, "t-" for tert, "i-" for iso) with a named alkyl group, then it is intended that the named alkyl group is an n-alkyl group (i.e., "propyl" is "n-propyl").

Certain alkyl groups defined herein may be "mono- or poly-substituted with —OH," meaning that one or more hydroxyl substituents is present on the alkyl group, and that each carbon atom available for substitution in the alkyl group may independently be unsubstituted or mono-substituted with hydroxyl provided that at least one carbon atom is substituted with hydroxyl. This encompasses alkyl groups where every available carbon atom is mono-substituted with hydroxyl as well as those where fewer than all available carbon atoms are mono-substituted with hydroxyl.

As used herein, "aryl" is intended to include phenyl (Ph), naphthyl, indenyl, tetrahydronaphthyl or indanyl. Phenyl is preferred.

Hydroxyl protecting groups may be used on intermediates during the synthetic procedures for making final products within the scope of this invention. Suitable protecting groups (designated as "PG" herein) for the hydroxyl groups, for example those in $R^{12}$ and $R^{13}$, include but are not limited to those that are known to be useful as hydroxyl protecting groups, such as for example benzyl, acetyl, benzoyl, tert-butyldiphenylsilyl, trimethylsilyl, para-methoxybenzyl, benzylidine, dimethylacetal and methoxy methyl. Conditions required to selectively add and remove such protecting groups are found in standard textbooks such as Greene, T, and Wuts, P. G. M., *Protective Groups in Organic Synthesis*, John Wiley & Sons, Inc., New York, N.Y., 1999.

Compounds of Formula I may contain one or more asymmetric centers and can thus occur as racemates and racemic mixtures, single enantiomers, enantiomeric mixtures, diastereomeric mixtures and individual diastereomers. All such isomeric forms of the compounds of Formula I are included within the scope of this invention. Furthermore, some of the crystalline forms for compounds of the present invention may exist as polymorphs and as such are intended to be included in the present invention. In addition, some of the compounds of the instant invention may form solvates with water or organic solvents. Such hydrates and solvates are also encompassed within the scope of this invention.

Due to their activity as cholesterol absorption inhibitors, the compounds of the present invention can be used in screening assays, where the assay is designed to identify new cholesterol absorption inhibitors. Radioactive isotopes of the compounds of Formula I are particularly useful in such assays, for example compounds of Formula I wherein sulfur is replaced with "hot" -$^{35}$S—, and particularly wherein the radioactive sulfur isotope is incorporated within the $R^9$ moiety. All such radioactive isotopes of the compounds of Formula I are included within the scope of this invention.

Reference to the compounds of this invention as those of "Formula I," "Formula Ia," and "Formula Ib" is intended herein to encompass compounds falling within the scope of each of these structural formulas including pharmaceutically acceptable salts and esters thereof where such salts and esters are possible. Herein, the term "pharmaceutically acceptable salts" means non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-ylmethylbenzimidazole, diethylamine, piperazine, morpholine, 2,4,4-trimethyl-2-pentamine and tris(hydroxymethyl)aminomethane.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

Pharmaceutically acceptable esters of available hydroxy or carboxylic acid groups can optionally be formed as well. Examples of pharmaceutically acceptable esters include, but are not limited to, —C1-4 alkyl and —C1-4 alkyl substituted with phenyl, dimethylamino and acetylamino.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by inhibition of cholesterol absorption.

The term "therapeutically effective amount" is intended to mean that amount of a pharmaceutical drug that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. Particularly, the dosage a patient receives can be selected so as to achieve the amount of LDL cholesterol lowering desired; the dosage a patient receives may also be titrated over time in order to reach a target LDL level. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition.

The compounds of the instant invention are cholesterol absorption inhibitors and are useful for reducing plasma cholesterol levels, particularly reducing plasma LDL cholesterol levels, when used either alone or in combination with another active agent, such as an anti-atherosclerotic agent, and more particularly a cholesterol biosynthesis inhibitor, for example an HMG-CoA reductase inhibitor. Thus the instant invention provides methods for inhibiting cholesterol absorption and for treating lipid disorders including hypercholesterolemia, comprising administering a therapeutically effective amount of a compound of Formula I to a person in need of such treatment. Further provided are methods for preventing or reducing the risk of developing atherosclerosis, as well as for halting or slowing the progression of atherosclerotic disease once it has become clinically evident, comprising the administration of a prophylactically or therapeutically effective amount, as appropriate, of a compound of Formula I to a mammal who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction are all clinical manifestations of atherosclerosis and are therefore encompassed by the terms "atherosclerosis" and "atherosclerotic disease."

A compound of Formula I may be administered to prevent or reduce the risk of occurrence, or recurrence where the potential exists, of a coronary heart disease event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a compound of Formula I to a patient at risk for such an event. The patient may or may not have atherosclerotic disease at the time of administration, or may be at risk for developing it.

Persons to be treated with the instant therapy include those at risk of developing atherosclerotic disease and of having an atherosclerotic disease event. Standard atherosclerotic disease risk factors are known to the average physician practicing in the relevant fields of medicine. Such known risk factors include but are not limited to hypertension, smoking, diabetes, low levels of high density lipoprotein (HDL) cholesterol, and a family history of atherosclerotic cardiovascular disease. Published guidelines for determining those who are at risk of developing atherosclerotic disease can be found in: Executive Summary of the Third Report of the National Cholesterol Education Program (NCEP) Expert Panel on Detection, Evaluation, and Treatment of High Blood Cholesterol in Adults (Adult Treatment Panel III), JAMA, 2001; 285 pp. 2486-2497. People who are identified as having one or more of the above-noted risk factors are intended to be included in the group of people considered at risk for developing atherosclerotic disease. People identified as having one or more of the above-noted risk factors, as well as people who already have atherosclerosis, are intended to be included within the group of people considered to be at risk for having an atherosclerotic disease event.

The oral dosage amount of the compound of Formula I is from about 0.1 to about 30 mg/kg of body weight per day, preferably about 0.1 to about 15 mg/kg of body weight per day. For an average body weight of 70 kg, the dosage level is therefore from about 5 mg to about 1000 mg of drug per day. However, dosage amounts will vary depending on factors as noted above, including the potency of the particular compound. Although the active drug of the present invention may be administered in divided doses, for example from two to four times daily, a single daily dose of the active drug is preferred. As examples, the daily dosage amount may be selected from, but not limited to, 5 mg, 10 mg, 15 mg, 20 mg, 25 mg, 40 mg, 50 mg, 75 mg, 80 mg, 100 mg and 200 mg.

The active drug employed in the instant therapy can be administered in such oral forms as tablets, capsules, pills, powders, granules, elixirs, tinctures, suspensions, syrups, and emulsions. Oral formulations are preferred, and particularly solid oral formulations such as tablets.

For compounds of Formula I, administration of the active drug can be via any pharmaceutically acceptable route and in any pharmaceutically acceptable dosage form. This includes the use of oral conventional rapid-release, time controlled-release and delayed-release (such enteric coated) pharmaceutical dosage forms. Additional suitable pharmaceutical compositions for use with the present invention are known to those of ordinary skill in the pharmaceutical arts; for example, see Remington's Pharmaceutical Sciences, Mack Publishing Co., Easton, Pa.

In the methods of the present invention, the active drug is typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with a non-toxic, pharmaceutically acceptable, inert carrier such as lactose, starch, sucrose, glucose, modified sugars, modified starches, methyl cellulose and its derivatives, dicalcium phosphate, calcium sulfate, mannitol, sorbitol and other reducing and non-reducing sugars, magnesium stearate, steric acid, sodium stearyl fumarate, glyceryl behenate, calcium stearate and the like. For oral administration in liquid form, the drug components can be combined with non-toxic, pharmaceutically acceptable inert carrier such as ethanol, glycerol, water and the like. Moreover, when desired or necessary, suitable binders, lubricants, disintegrating agents and coloring and flavoring agents can also be incorporated into the mixture. Stabilizing agents such as antioxidants, for example butylated hydroxyanisole (BHA), 2,6-di-tert-butyl-4-methylphenol (BHT), propyl gallate, sodium ascorbate, citric acid, calcium metabisulphite, hydroquinone, and 7-hydroxycoumarin, particularly BHA, propyl gallate and combinations thereof, can also be added to stabilize the dosage forms. When a compound of Formula I is formulated together with an HMG-CoA reductase inhibitor such as simvastatin, the use of at least one stabilizing agent is preferred in the composition. Other suitable components include gelatin, sweeteners, natural and synthetic gums such as acacia, tragacanth or alginates, carboxymethylcellulose, polyethylene glycol, waxes and the like.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier.

One or more additional active agents may be administered in combination with a compound of Formula I, and therefore an embodiment of the instant invention encompasses a drug combination. The drug combination encompasses a single dosage formulation comprised of the compound of Formula I and additional active agent or agents, as well as administration of each of the compound of Formula I and the additional active agent or agents in separate dosage formulations, which allows for concurrent or sequential administration of the active agents. The additional active agent or agents can be lipid modifying agents, particularly a cholesterol biosynthesis inhibitor such as an HMG-CoA reductase inhibitor, or agents having other pharmaceutical activities, or agents that have both lipid-modifying effects and other pharmaceutical activities. Examples of HMG-CoA reductase inhibitors useful for this purpose include statins in their lactonized or dihydroxy open acid forms and pharmaceutically acceptable salts and esters thereof, including but not limited to lovastatin (MEVACOR®; see U.S. Pat. No. 4,342,767); simvastatin (ZOCOR®; see U.S. Pat. No. 4,444,784); dihydroxy open-acid simvastatin, particularly the ammonium or calcium salts thereof; pravastatin, particularly the sodium salt thereof (PRAVACOL®; see U.S. Pat. No. 4,346,227); fluvastatin particularly the sodium salt thereof (LESCOL®; see U.S. Pat. No. 5,354,772); atorvastatin, particularly the calcium salt thereof (LIPITOR®; see U.S. Pat. No. 5,273,995); rosuvastatin (CRESTOR®; see U.S. Pat. No. 5,260,440); and pitavastatin also referred to as NK-104 (see PCT international publication number WO 97/23200). Examples of additional active agents which may be employed include but are not limited to one or more of FLAP inhibitors; 5-lipoxygenase inhibitors; additional cholesterol absorption inhibitors such as ezetimibe (ZETIA®), described in U.S. Pat. Nos. Re. 37,721 and 5,846,966; cholesterol ester transfer protein (CETP) inhibitors, for example JTT-705 and torcetrapib, also known as CP529,414; HMG-CoA synthase inhibitors; squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT1 and -2; microsomal triglyceride transfer protein (MTP) inhibitors; niacin; niacin receptor agonists such as acipimox and acifran, as well as niacin receptor partial agonists; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors such as enalapril and captopril; calcium channel blockers such as nifedipine and diltiazam; endothelian antagonists; agents that enhance ABC1 gene expression; FXR ligands including both inhibitors and agonists; and LXR ligands including both inhibitors and agonists of all sub-types of this receptor, e.g. LXRα and LXRβ; bisphosphonate compounds such as alendronate sodium; and cyclooxygenase-2 inhibitors such as rofecoxib, celecoxib and valdecoxib.

A therapeutically or prophylactically effective amount, as appropriate, of a compound of Formula I can be used for the preparation of a medicament useful for inhibiting cholesterol absorption, as well as for treating and/or reducing the risk for diseases and conditions affected by inhibition of cholesterol absorption, such as treating lipid disorders, preventing or reducing the risk of developing atherosclerotic disease, halting or slowing the progression of atherosclerotic disease once it has become clinically manifest, and preventing or reducing the risk of a first or subsequent occurrence of an atherosclerotic disease event. For example, the medicament may be comprised of about 5 mg to about 1000 mg of a compound of Formula I. The medicament comprised of a compound of Formula I may also be prepared with one or more additional active agents, such as those described supra.

Compounds of this invention were determined to inhibit cholesterol absorption employing the Cholesterol Absorption Assay in Mice, below. This assay involves comparing a test compound to ezetimibe with respect to their ability to inhibit cholesterol absorption in mice. Both ezetimibe and the tested compounds of this invention inhibited cholesterol absorption by >90% at the highest dose tested. The tested compounds had an ID 50<1 mg/kg.

Cholesterol Absorption Assay in Mice: C57BL/6 male mice (n=6/group), aged 10-14 weeks, were dosed orally with 0.2 ml 0.25% methyl cellulose solution with or without test compound or ezetimibe (0.12-10 mg/kg). Thirty minutes later all of the mice were dosed orally with 0.2 ml INTRALIPID™ containing 2 μCi [$^3$H]-cholesterol per mouse. Five hours later, the animals were euthanized, and liver and blood were collected. Cholesterol counts in liver and plasma were determined, and percent inhibition of cholesterol absorption was calculated.

The compounds of structural Formula I of the present invention can be prepared according to the procedures of the following Scheme and Examples, using appropriate materials, and are further exemplified by specific examples which follow. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds.

A variety of chromatographic techniques may be employed in the preparation of the compounds. These techniques include, but are not limited to: High Performance Liquid Chromatography (HPLC) including normal-reversed- and chiral-phase; Medium Pressure Liquid Chromatography (MPLC), Super Critical Fluid Chromatography; preparative Thin Layer Chromatography (prep TLC); flash chromatography with silica gel or reversed-phase silica gel; ion-exchange chromatography; and radial chromatography. All temperatures are degrees Celsius unless otherwise noted.

| Some abbreviations used herein include: | |
|---|---|
| Ac | Acyl ($CH_3C(O)$—) |
| Aq. | Aqueous |
| Bn | Benzyl |
| C. | Celsius |
| calc. | Calculated |
| DCM | dichloromethane |

Some abbreviations used herein include:

| | |
|---|---|
| DIEA | N,N-diisopropylethylamine |
| DMAP | 4-dimethylaminopyridine |
| DMF | N,N-dimethylformamide |
| equiv. | Equivalent(s) |
| ES-MS | Electron Spray Ion-Mass Spectroscopy |
| EtOAc | Ethyl acetate |
| h | Hour(s) |
| HPLC | High performance liquid chromatography |
| min | Minute(s) |
| mp | Melting point |
| MS | Mass spectrum |
| Prep. | Preparative |
| r.t. (or rt) | Room temperature |
| sat. | Saturated |
| TBAI | tetrabutylammonium iodide |
| TBS | Tert-butyl dimethylsilyl |
| TEA | Triethyl amine |
| TFA | Trifluoroacetic acid |
| THF | Tetrahydrofuran |
| TLC | Thin layer chromatography |

The general Schemes below illustrate a method for the syntheses of compounds of the present invention. All substituents and variables (e.g., $R^1$, $R^2$, $Ar^1$, v, w, etc.) are as defined above in Formula I unless indicated otherwise.

In Scheme I, I-1 is treated with a terminal alkyne of type I-2 in the presence of a suitable palladium catalyst such as tetrakistriphenylphosphine palladium(0) or [1,1'-bis(diphenylphosphino)ferrocene]dichloropalladium(II) or the like, and copper(I) iodide. The reaction is usually performed in an inert organic solvent such as DMF, between room temperature and 100° C., for a period of 6-48 h, and the product is an internal alkyne of structural formula I-3. Alkyne I-2 may contain a radioactive atom such as $^{35}S$ to provide the corresponding radiolabeled adduct upon reaction with I-1. Conversion of I-3 to I-4 can be achieved by hydrogenation of the triple bond in the $R^9$ position, followed by treatment with guanidine and triethylamine in methanol to selectively remove the phenolic acetate; then converting the phenol to the triflate I-4 via treatment with bis(trifluoromethylsulfonyl) amino pyridine in the presence of either triethylamine or N,N diisopropyl-N-ethyl amine in dichloromethane medium. Incorporation of the alkynyl-$R^{12a}$ group is achieved by palladium assisted coupling of the triflate I-4 with either hydroxyl-protected or unprotected alkynyl-$R^{12a}$ derivative I-5. Examples of hydroxyl protecting groups (PG) include, for example, benzyl, acetate, acetal or any other suitable oxygen protecting group, or combinations thereof, compatible with earlier or subsequent chemical reactions. As an example, $R^{12a}$ includes but is not limited to —$C_{1-6}$alkyl-OBn and

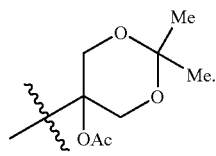

In this method, I-4 is treated with an alkynyl-$R^{12a}$ of type I-5 in the presence of a suitable palladium catalyst such as tetrakistriphenylphosphine palladium(0) and copper(I) iodide with an initiator such as tetrabutylammonium iodide. The reaction is usually performed in an inert organic solvent such as DMF, at 50° C., for a period of 1 to 5 hrs, and the product possesses an alkynyl-$R^{12a}$ of structure I-6. Hydrogenation of the triple bond occurs along with the removal of any benzyl protecting groups contained in $R^{12a}$ by treatment with 10% palladium on carbon catalyst under hydrogen atmosphere in a solvent such as ethyl acetate reacting over 15-24 hours to form I-7. Hydrolysis or cleavage of any remaining hydroxyl protecting groups may be performed at this time, or non-benzylic protecting groups can be removed prior to the hydrogenation step. For example, diols protected as acetals that are contained in $R^{12a}$ may be removed by treatment with aqueous acid. When $R^{12a}$ contains one or more acetate groups, deprotection with potassium cyanide in methanol heated to 50° C. for 1-2 hours affords the free hydroxyl groups.

SCHEME I

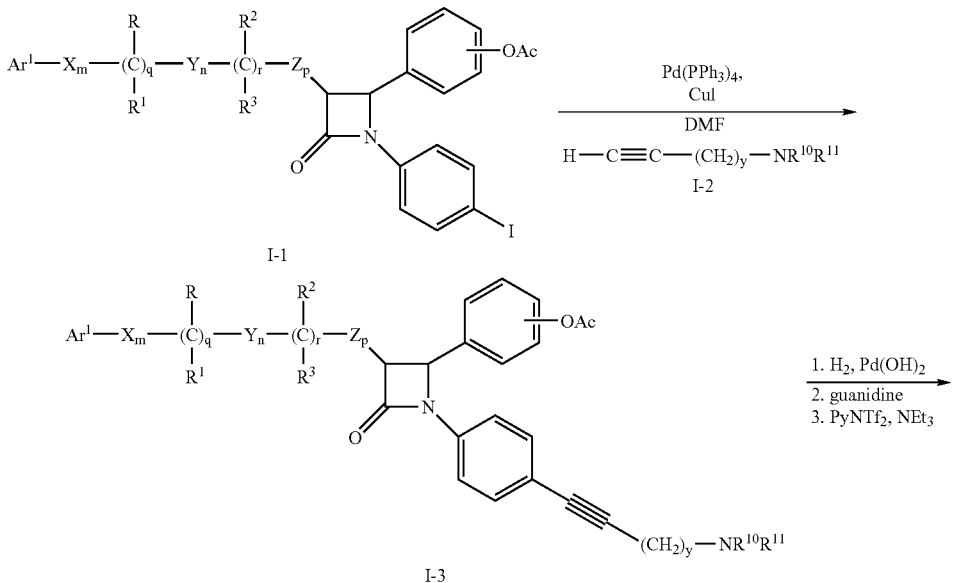

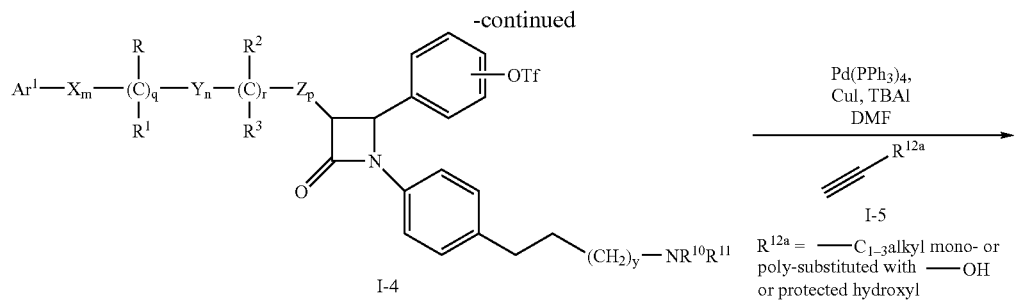

I-4

$R^{12a}$ = —$C_{1-3}$alkyl mono- or poly-substituted with —OH or protected hydroxyl

I-5

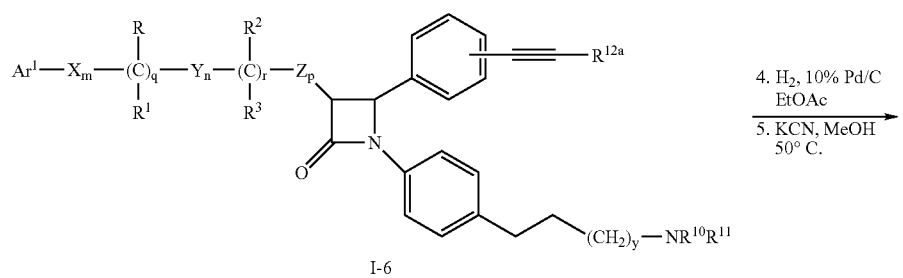

I-6

4. $H_2$, 10% Pd/C EtOAc
5. KCN, MeOH 50° C.

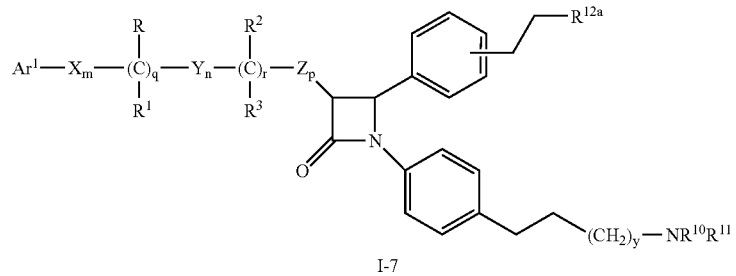

I-7

The preparation of compounds possessing a 2-hydroxyphenyl group in the final product I-12 is outlined in Scheme II. The bis(benzyloxy)intermediate I-8 may be treated with a terminal alkyne of type I-2 in the presence of a suitable palladium catalyst such as tetrakistriphenylphosphine palladium(0) or [1,1′-bis(diphenylphosphino)ferrocene]dichloropalladium(II) or the like, and copper(I) iodide. The reaction is usually performed in an inert organic solvent such as DMF, between room temperature and 100° C., for a period of 648 h, and the product is an internal alkyne of structural formula I-9.

Alkyne I-2 may contain a radioactive atom such as $^{35}$S to provide the corresponding radiolabeled adduct upon reaction with I-8. Conversion of I-9 to I-10 can be achieved by hydrogenation of the triple bond, with concomitant selective hydrogenolysis of the benzyl ether which is not at the 2-position, followed by converting the resulting phenol to the triflate I-10 via treatment with triflic anhydride (trifluoromethanesulfonic acid anhydride) in the presence of pyridine in dichloromethane medium. The remaining steps can be performed as described in Scheme I.

SCHEME II

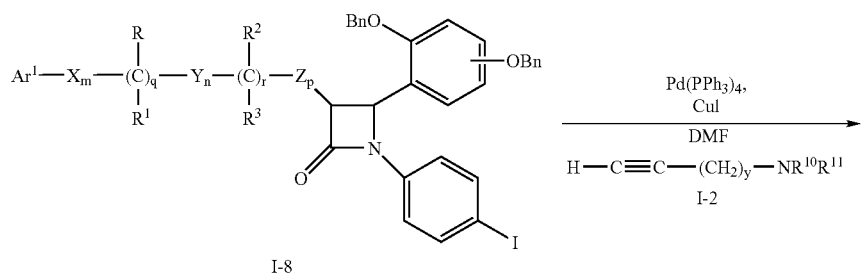

I-8

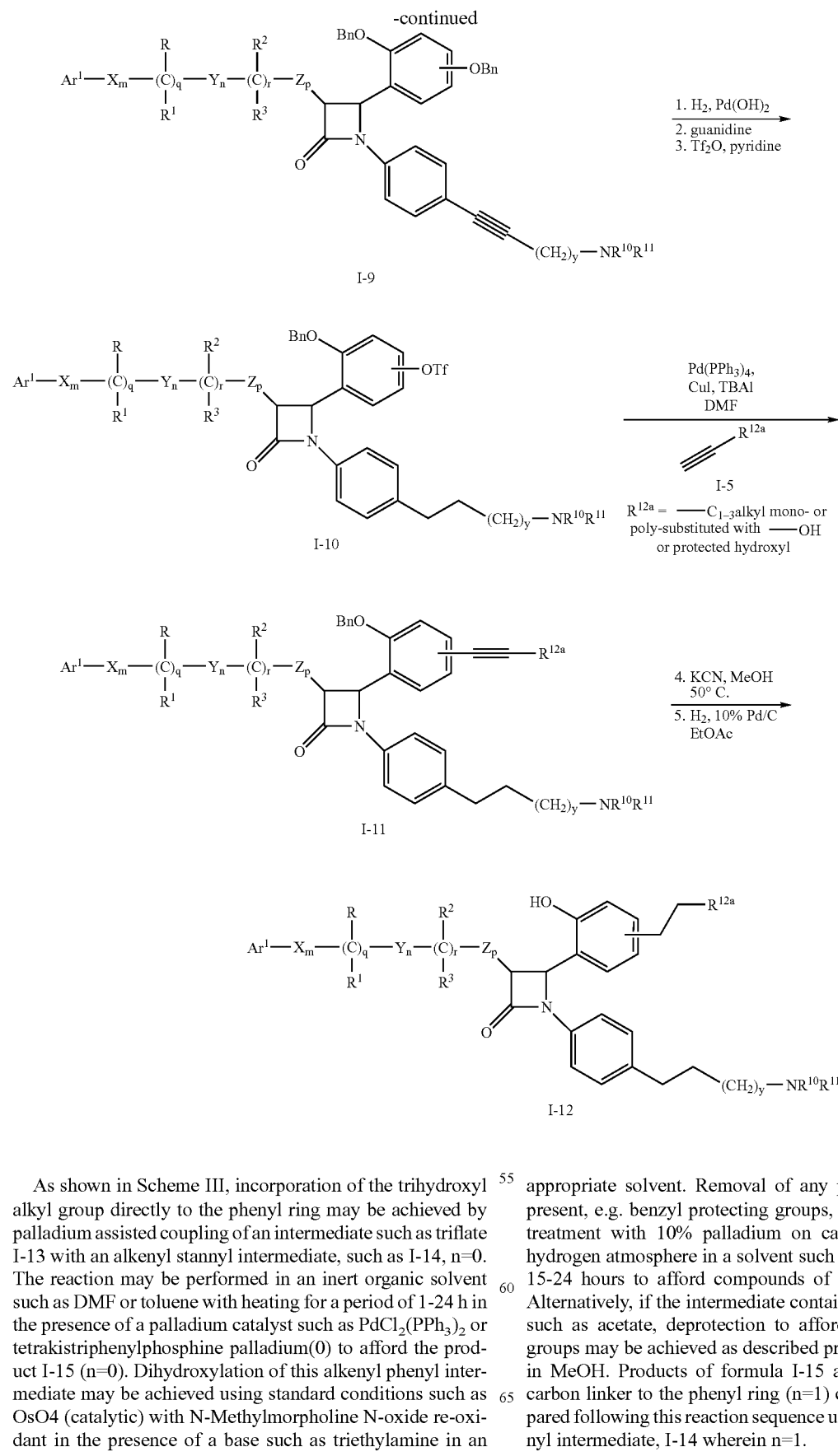

As shown in Scheme III, incorporation of the trihydroxyl alkyl group directly to the phenyl ring may be achieved by palladium assisted coupling of an intermediate such as triflate I-13 with an alkenyl stannyl intermediate, such as I-14, n=0. The reaction may be performed in an inert organic solvent such as DMF or toluene with heating for a period of 1-24 h in the presence of a palladium catalyst such as $PdCl_2(PPh_3)_2$ or tetrakistriphenylphosphine palladium(0) to afford the product I-15 (n=0). Dihydroxylation of this alkenyl phenyl intermediate may be achieved using standard conditions such as $OsO_4$ (catalytic) with N-Methylmorpholine N-oxide re-oxidant in the presence of a base such as triethylamine in an appropriate solvent. Removal of any protecting groups if present, e.g. benzyl protecting groups, may be achieved by treatment with 10% palladium on carbon catalyst under hydrogen atmosphere in a solvent such as ethyl acetate over 15-24 hours to afford compounds of formula I-16 (n=0). Alternatively, if the intermediate contains protecting groups such as acetate, deprotection to afford the free hydroxyl groups may be achieved as described previously using KCN in MeOH. Products of formula I-15 and I-16 with a one carbon linker to the phenyl ring (n=1) can similarly be prepared following this reaction sequence using the alkenyl stannyl intermediate, I-14 wherein n=1.

SCHEME III

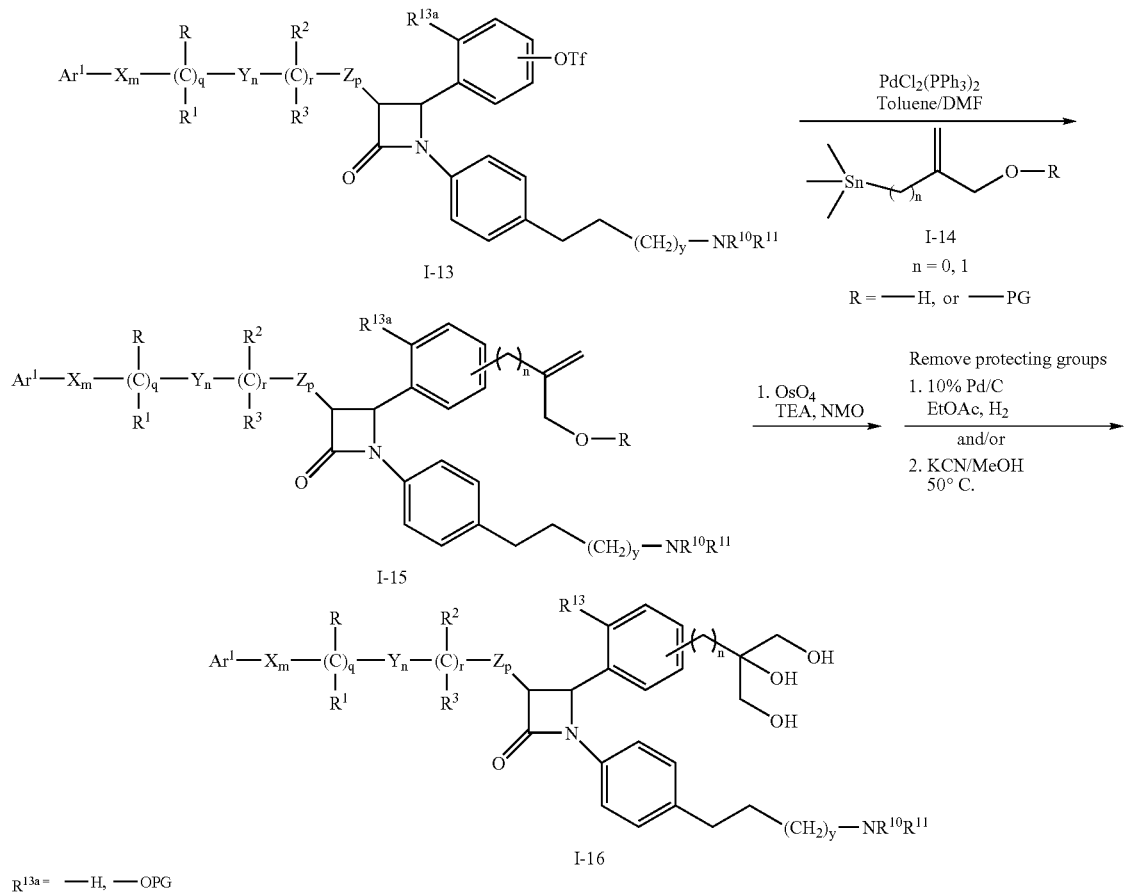

$R^{13a}$ = —H, —OPG

As shown in Scheme IV, compounds containing a 2-carbon linker to the functionalized nitrogen group may be obtained by treating the alkenyl intermediate I-17 with 9-borabicyclo[3.3.1]nonane (9-BBN) to form the alkyl borate ester, which upon palladium catalyzed cross-coupling with the iodide I-18 may afford the intermediate I-19 possessing a 2-carbon-linked nitrogen functional group. Intermediate I-19 may be deprotected and then converted to functionalized nitrogen intermediates using procedures as described herein and those known in the art for sulfonamide formation, carboxamide formation, etc. Subsequent intermediates may then be converted to compounds of the present invention using procedures similar to those previously described above and in Schemes I, II and III.

SCHEME IV

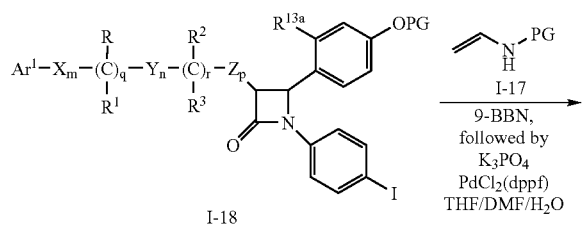

-continued

[structure I-19]

$R^{13a}$ = —H, —OPG

As shown in Scheme V, in a related fashion, compounds containing a one carbon linker may be obtained by treating iodo intermediate I-18 with reagents capable of aryl cyanation such as trimethylsilylcyanide (TMS-CN) and a palladium catalyst to afford aryl cyanide intermediates. This cyano-intermediate may be hydrogenated in the presence of Raney-Nickel catalyst to afford the desired aminomethyl intermediate I-19 with one carbon-linked nitrogen group. This intermediate may then be converted to functionalized nitrogen intermediates using procedures as described herein and those known in the art for sulfonamide formation, carboxamide formation, etc. Further manipulation of compounds of formula I-19 may be achieved by sequence similar to those described in Schemes I-III to make compounds of Formula I.

SCHEME V

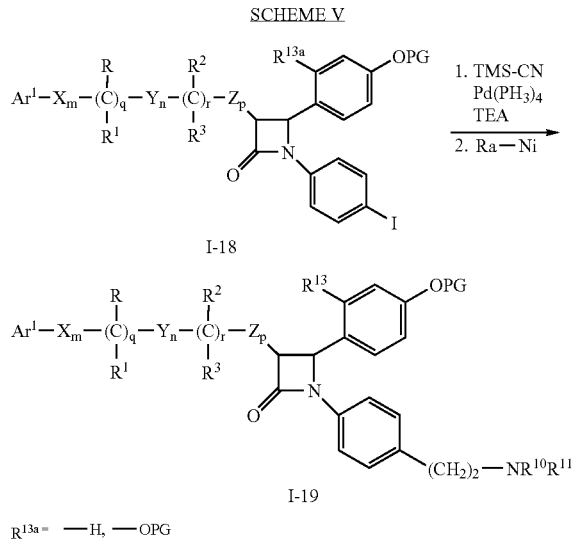

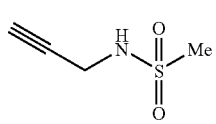

The following examples are provided to illustrate the invention and are not to be construed as limiting the scope of the invention in any matter. Within the following synthetic examples, reference to an intermediate from a prior step is a reference to an intermediate compound made in a prior step within the same example, unless otherwise noted. The following designations are used in the Examples for certain repetitively used intermediates:

Preparation of N-prop-2-yn-1-ylmethanesulfonamide (i-1)

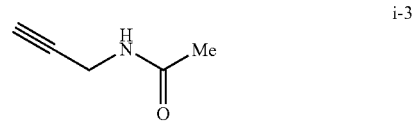

Methansulfonylchloride (1.40 mL, 18.1 mmol) was added dropwise to a stirred solution of propargylamine (1.00 g, 18.1 mmol) and dimethylaminopyridine (44.0 mg, 0.36 mmol) in pyridine (10 mL) at 0° C. After aging for approximately 15 h, the reaction mixture was poured into 1N HCl and extracted twice with ethyl acetate. The combined organic extracts were washed with saturated aqueous sodium bicarbonate, brine, dried (MgSO$_4$), filtered and concentrated in vacuo, to afford the title compound i-1. Crude i-1 crystallized on standing and was used without further purification. $^1$HNMR (500 MHz, CDCl$_3$) δ: 4.92 (br s, 1H), 3.99 (dd, J=2.3, 6.2 Hz, 2H), 3.11 (s, 3H), 2.70 (br t, J=2.3 Hz).

Preparation of N-Methyl-N-prop-2-yn-1-ylmethanesulfonamide (i-2)

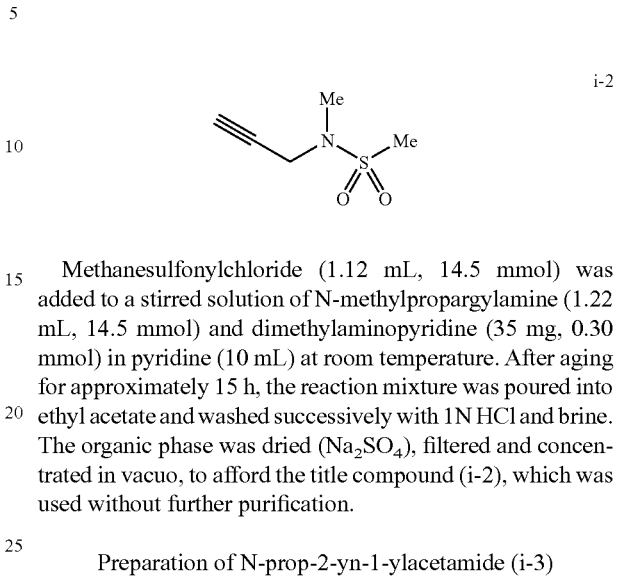

Methanesulfonylchloride (1.12 mL, 14.5 mmol) was added to a stirred solution of N-methylpropargylamine (1.22 mL, 14.5 mmol) and dimethylaminopyridine (35 mg, 0.30 mmol) in pyridine (10 mL) at room temperature. After aging for approximately 15 h, the reaction mixture was poured into ethyl acetate and washed successively with 1N HCl and brine. The organic phase was dried (Na$_2$SO$_4$), filtered and concentrated in vacuo, to afford the title compound (i-2), which was used without further purification.

Preparation of N-prop-2-yn-1-ylacetamide (i-3)

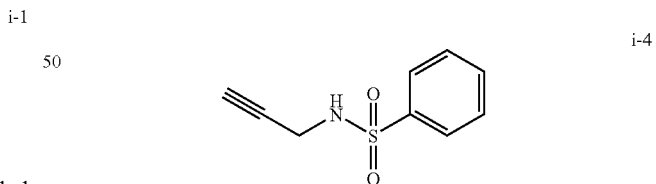

Acetyl chloride (0.52 mL, 7.3 mmol) was added to a stirred solution of propargylamine (0.5 mL, 7.3 mmol) and dimethylaminopyridine (18 mg, 0.14 mmol) in pyridine (2.5 mL) at 0° C., and the resulting mixture was allowed to warm to ambient temperature. After approximately 15 h, the reaction mixture was diluted with ethyl acetate and washed successively with 1N HCl and brine. The organic phase was dried (Na$_2$SO$_4$), filtered and concentrated in vacuo to afford the title compound (i-3), which was used without further purification.

Preparation of N-prop-2-yn-1-ylbenzenesulfonamide (i-4)

Benzene sulfonyl chloride (1.16 mL, 9.1 mmol) was added to stirred solution of propargylamine (0.62 mL, 9.1 mmol) and dimethylaminopyridine (22 mg, 0.18 mmol) in pyridine (5 mL) at room temperature. The resulting solution was aged at ambient temperature for approximately 15 h. The reaction mixture was diluted with ethyl acetate and washed successively with 1N HCl and brine. The organic phase was dried (Na$_2$SO$_4$), filtered and concentrated in vacuo to furnish the title compound (i-4), which was used without further purification.

Preparation of N,N-Dimethyl-N'-prop-2-yn-1-ylurea (i-5)

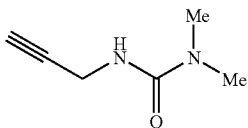

Dimethyl carbamylchloride (0.84 mL, 9.1 mmol) was added to a stirred solution of propargylamine (0.62 mL, 9.1 mmol) and dimethylaminopyridine (22 mg, 0.18 mmol) in pyridine (5 mL) at room temperature. The resulting suspension was stirred at ambient temperature for approximately 15 h. The reaction mixture was diluted with ethyl acetate and washed successively with 1N HCl and brine. The organic phase was dried ($Na_2SO_4$), filtered and concentrated in vacuo to afford the title compound (i-5), which was used without further purification.

Preparation of 5-ethynyl-2,2-dimethyl-1,3-dioxan-5-yl acetate (i-6)

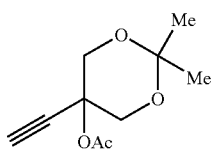

To a dry 250 mL roundbottom flask was charged with a 0.5M solution of ethynylmagnesium bromide in THF (115 mL, 57.7 mmol) under nitrogen atmosphere. The resulting solution was cooled to 0° C. in an ice bath. To the cooled solution was added slowly a solution of 2,2-dimethyl-1,3-dioxane-5-one (5 g, 38.44 mmol) in 50 mL dry THF. The ice bath was removed and the resulting reaction mixture was stirred at ambient temperature for 1.5 hrs. The reaction mixture was quenched with sat. aq. $NH_4Cl$ (50 mL) and then extracted with ethyl acetate (100 mL). The organic layer was dried over $Na_2SO_4$, filtered and the solvent removed under vacuum to afford the crude intermediate.

The crude intermediate was dissolved in $CH_2Cl_2$ (100 mL) under nitrogen atmosphere. To the resulting solution was added simultaneously by syringe acetic anhydride (4.34 mL, 46 mmol) and TEA (6.4 mL, 46 mmol). To the reaction mixture was added DMAP (0.56 g, 4.6 mmol). The reaction mixture was stirred for 3 hrs at room temperature at which time the reaction was quenched by the addition of 1N aq. HCl (100 mL). The reaction mixture was transferred to separatory funnel and the organic layer was separated. The organic layer was washed with aq. $NaHCO_3$ (100 mL), water (50 mL), brine, dried, filtered and the solvent removed under vacuum to afford the title compound (i-6) which was used without further purification. $^1$HNMR (500 MHz, $CDCl_3$) δ: 4.14 (d, J=12.6, 2H) 4.07 (d, J=12.6 Hz, 2H), 2.65 (s, 1H), 2.12 (s, 3H), 1.45 (s, 3H), 1.41 (s, 3H).

The compound (3R,4S)-3-[(3S)-3-(4-fluorophenyl)-3-hydroxypropyl]-4-(4-hydroxyphenyl)-1-(4-iodophenyl)azetidin-2-one (i-7) and (1-7a) were prepared according to Burnett, D. S.; Caplen, M. A.; Domalski, M. S.; Browne, M. E.; Davis, H. R. Jr.; Clader, J. W. *Bioorg. Med. Chem. Lett.* (2002), 12, 311. Compound i-8 is the dihydroxy-protected analog of i-7, where the protecting groups are acetyl.

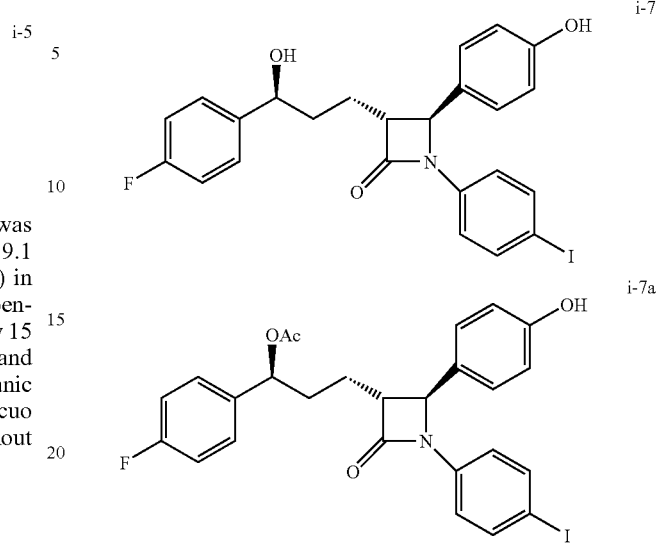

Preparation of 4-[(2S,3R)-3-[(3S)-3-(acetyloxy)-3-(4-fluorophenyl)propyl]-1-(4-iodophenyl)-4-oxoazetidin-2-yl]phenyl acetate (i-8)

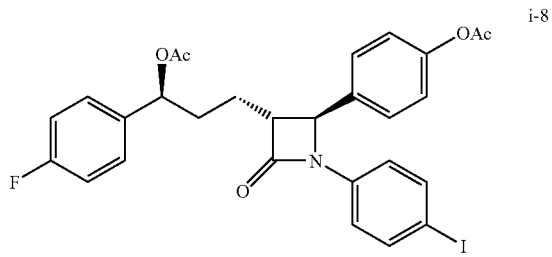

To a solution of (1S)-1-(4-fluorophenyl)-3-[(2S,3R)-2-(4-hydroxyphenyl)-1-(4-iodophenyl)-4-oxoazetidin-3-yl]propyl acetate (1-7a) (2 g, 3.58 mmol) (prepared according to Burnett, D. S.; Caplen, M. A.; Domalski, M. S.; Browne, M. E.; Davis, H. R. Jr.; Clader, J. W. *Bioorg. Med. Chem. Lett.* (2002), 12, 311) in $CH_2Cl_2$ (25 mL) under nitrogen atmosphere was added acetic anhydride (0.4 mL, 4.30 mmol), triethylamine (0.75 mL, 5.38 mmol) and DMAP. The reaction mixture was stirred at RT for 1 hr and the solvent removed under vacuum. The residue was purified by MPLC (silica column) with stepwise gradient elution; (0-100% EtOAc/hexanes as eluent) to afford the title compound (i-8). m/z (ES) (M-OAc)$^+$. $^1$HNMR (500 MHz, $CDCl_3$) δ: 7.57 (d, J=8.6, 1H) 7.38-7.26 (m, 5H), 7.22 (br d, J=7.1 H, 2H), 7.14 (d, J=8.5 Hz, 1H), 7.08-7.02 (m, 3H), 5.74 (t, J=6.7 Hz, 1H), 4.62 (d, J=2.3 Hz, 1H), 3.10 (dt, J=2.3, 7.8 Hz, 1H), 2.34 (s, 3H), 2.08 (s, 3H), 2.09-2.03 (m, 2H), 1.94-1.86 (m, 2H).

Adiitional intermediates described in the Examples:

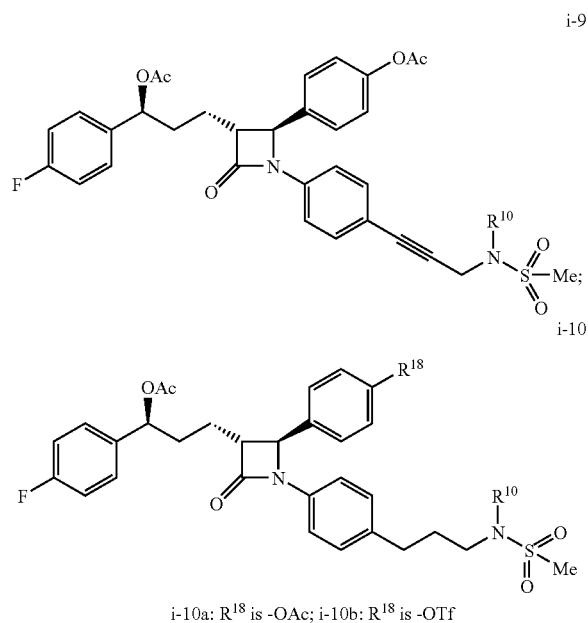

i-9

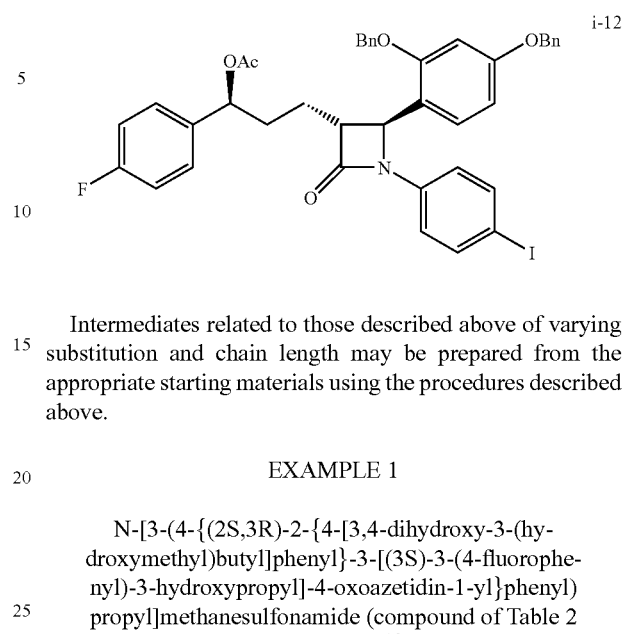

i-12

Intermediates related to those described above of varying substitution and chain length may be prepared from the appropriate starting materials using the procedures described above.

EXAMPLE 1

N-[3-(4-{(2S,3R)-2-{4-[3,4-dihydroxy-3-(hydroxymethyl)butyl]phenyl}-3-[(3S)-3-(4-fluorophenyl)-3-hydroxypropyl]-4-oxoazetidin-1-yl}phenyl)propyl]methanesulfonamide (compound of Table 2 wherein y is 1 and $R^{10}$ is —H)

Step A: Preparation of 4-[(2S, 3R)-3-[(3S)-3-(acetyloxy)-3-(4-fluorophenyl)propyl]-1-(4-{3-[(methylsulfonyl)amino]prop-1-yn-1-yl}phenyl)-4-oxoazetidin-2-yl]phenyl acetate (i-9 wherein $R^{10}$ is —H)

i-10a: $R^{18}$ is -OAc; i-10b: $R^{18}$ is -OTf

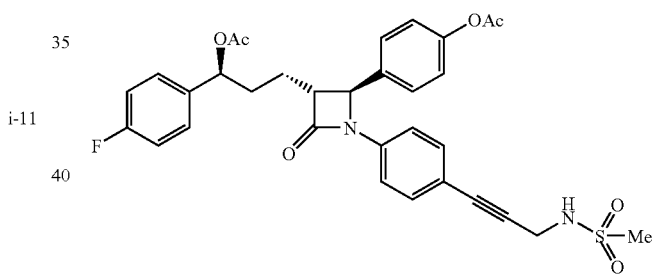

Preparation of [(hex-5-yn-1-yloxy)methyl]benzene or benzyl hex-5-yn-1-yl ether (i-11)

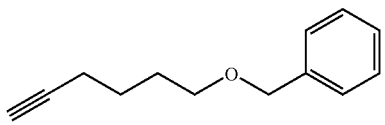

i-11

To a solution of 5-hexyn-1-ol (1.17 g, 11.88 mmol) in anhydrous DMF (100 mL) under nitrogen atmosphere was added TBAI (0.87 g, 2.38 mmol) followed by 60% NaH dispersion in oil (0.55 g, 14.26 mmol) in portions over 0.5 h. The reaction mixture was stirred for 0.5 hr at which time benzyl bromide (2.44 g, 14.26 mmol) was added by syringe. The reaction mixture was stirred for 16 h at room temperature at which time the reaction was quenched by the addition of sat. aq. NH$_4$Cl (100 mL). The reaction mixture was transferred to separatory funnel and extracted with ether (3×75 mL). The combined organic extracts were washed with water (50 mL), brine (75 mL), dried (Na$_2$SO$_4$), filtered and the solvent removed under vacuum. The residue was purified by MPLC (silica column) with stepwise gradient elution (0-60% EtOAc/hexanes as eluent) to afford the title compound (i-11).

(1S)-3-[(2S,3R)-2-[2,4-bis(benzyloxy)phenyl]-1-(4-iodophenyl)-4-oxoazetidin-3-yl]-1-(4-fluorophenyl)propyl acetate (i-12) was prepared from 2,4-bisbenzyloxyacetaldehyde and 4-iodoaniline using procedures as described in Vaccaro, W. D. et al., Bioorg. Med. Chem., vol. 6 (1998), 1429-1437.

Dichlorobis(triphenylphosphine)palladium(II) (1.27 g, 1.68 mmol) and copper(I) iodide (632 mg, 3.32 mmol) were added to a solution of i-8 (10.0 g, 16.6 mmol) and i-1 (3.34 g, 25.0 mmol) in triethylamine (16.2 mL, 116.34 mmol) and DMF (150 mL). The reaction mixture was saturated with nitrogen and stirred at room temperature. After 2 h, the reaction mixture was partitioned between 400 mL EtOAc and 250 mL water. The organic layer was washed with water (150 mL), brine (150 mL), dried (MgSO$_4$), filtered and concentrated in vacuo. Purification of the crude residue by MPLC (silica column) with stepwise gradient elution; (0-100% EtOAc/hexanes as eluent) afforded the title compound. m/z (ES) 629 (M+Na)$^+$, 547 (M-OAc)$^+$. $^1$HNMR (500 MHz, CDCl$_3$) δ: 7.35 (d, J=8.4 Hz, 1H), 7.28 (dd, J=6.4, 8.4 Hz, 1H), 7.19 (d, J=8.5 Hz, 1H), 7.12 (d, J=8.5 Hz, 1H), 7.08 (d, J=8.3 Hz, 1H), 7.02 (dd, J=6.5, 8.6 Hz, 1H), 5.72 (t, 6.6 Hz, 1H), 4.60 (d, J=2.3 Hz, 1H), 4.21-4.16 (m, 1H), 4.15 (overlapped dd, J=7.1, 11 Hz, 1H), 3.15-3.12 (m, 2H), 3.09-3.04 (m, 1H), 2.96 (s, 3H), 2.58 (t, 7.6 Hz, 2H), 2.30 (s, 3H), 2.07 (overlapped s, 3H), 2.09-2.03 (m, 2H), 1.90-1.83 (m, 4H).

Step B: Preparation of 4-[(2S,3R)-3-[(3S)-3-(acetyloxy)-3-(4-fluorophenyl)propyl]-1-(4-{3-[(methylsulfonyl)amino]propyl}phenyl)-4-oxoazetidin-2-yl] phenyl acetate (i-10a wherein R[10] is —H)

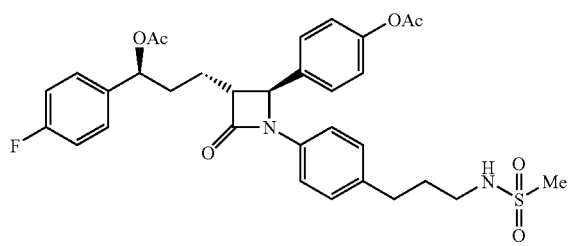

A mixture of the intermediate from Step A (8.5 g, 14 mmol) and 10% palladium on activated carbon (2.2 g) in ethanol (100 mL) and EtOAc (150 mL) was hydrogenated at atmospheric pressure. After 15 h, the reaction mixture was filtered through MgSO4 and filter aid and the filtered catalyst washed several times with EtOAc. The filtrate was concentrated in vacuo to afford the title compound which was used without further purification. m/z (ES) 663 (M+Na)$^+$, 551 (M-OAc)$^+$.

Step C: Preparation of (1S)-1-(4-fluorophenyl)-3-[(3R,4S)-1-(4-{3-[(methylsulfonyl)amino] propyl}phenyl)-2-oxo-4-(4-{[(trifluoromethyl)-sulfonyl]oxy}phenyl)azetidin-3-yl]propyl acetate (i-10a wherein R[10] is —H)

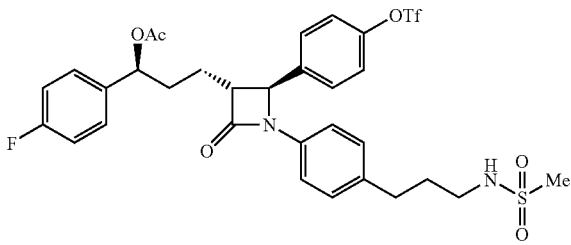

Guanidine hydrochloride (1.34 g, 13.93 mmol) was added to a mixture of the intermediate from Step B, (8.5 g, 13.93 mmol) and triethylamine (1.95 mL, 13.93 mmol) in methanol (150 mL). After 3 h, the solvent was removed under vacuum and the residue was dissolved in EtOAc (200 mL)/water (100 mL) and 2N aq. HCl. The mixture was transferred to a separatory funnel and the layers separated. The organic layer was washed with brine (100 mL), dried (MgSO$_4$), filtered and concentrated in vacuo to afford a clear oil.

The crude intermediate was dissolved in methylene chloride (100 mL) and to the solution was added (bis(trifluoromethylsulfonyl)amino pyridine (8.14 g, 13.93 mmol), triethylamine (1.95 mL, 13.93 mmol), DMAP (~100 mg, catalytic). The resulting solution was stirred for 2 h at room temperature. The reaction was quenched with 1N aq. HCl and the organic layer was separated. The organic extract was washed with brine, dried (MgSO$_4$) and concentrated in vacuo. Purification of the crude residue by MPLC (silica column) with stepwise gradient elution (0-100% EtOAc/hexanes as eluent) afforded the title compound. m/z (ES) 723 (M+Na)$^+$, 641 (M-OAc)$^+$.

Step D: Preparation of (1S)-3-[(2S,3R)-2-(4-{[5-(acetyloxy)-2,2-dimethyl-1,3-dioxan-5-yl] ethynyl}phenyl)-1-(4-{3-[(methylsulfonyl)amino] propyl}phenyl)-4-oxoazetidin-3-yl]-1-(4-fluorophenyl)propyl acetate

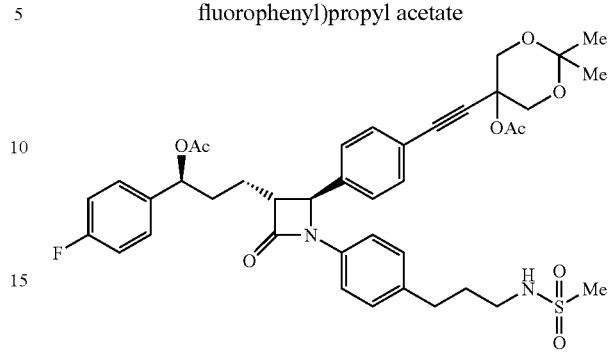

To an oven dried flask 250 mL flask was added CuI (300 mg, 1.44 mmol), tetrabutylammonium iodide (TBAI, 1.58 g, 4.28 mmol). The charged flask was set under nitrogen atmosphere and a solution of the intermediate from Step C, (3.5 g, 4.28 mmol) in 30 mL anhydrous DMF was added to the flask. A solution of 5-ethynyl-2,2-dimethyl-1,3-dioxan-5-yl acetate (i-6) (1.70 g, 8.56 mmol) in DMF (20 mL) was added to the mixture. The flask was then equipped with a condenser, and the mixture was evacuated and set under nitrogen several times to degas the solvent. Solid Pd(PPh$_3$)$_4$ (3.32 g, 3 mmol) was then added to the reaction followed by TEA (4.2 mL, 30 mmol). The reaction mixture was heated to 70° C. for 2 hours during which time the reaction mixture became dark brown in color. The reaction was removed from the heating bath, cooled and partitioned with EtOAc (250 mL) and 1N aq. HCl (100 mL). The organic layer was washed with water (100 mL), brine (75 mL), dried over magnesium sulfate, filtered and concentrated under vacuum. The residue was purified by MPLC (silica column) with stepwise gradient elution; (0-100% EtOAc/hexanes as eluent) to afford the title compound. m/z (ES) 689 (M-OAc)$^+$. $^1$HNMR (500 MHz, CD$_3$OD) δ: 7.44 (d, J=8.3 Hz, 1H), 7.38-7.32 (m, 4H), 7.16 (d, J=8.5 Hz, 2H), 7.10 (d, J=8.5 Hz, 2H), 7.06 (t, J=8.6 Hz, 2H), 5.70 (app t, 6.3 Hz, 1H 4.20 (s, 3H), 3.10-3.05 (m, 1H), 3.02 (d, J=7.0 Hz, 2H), 2.89 (s, 3H), 2.60 (t, 7.4 Hz, 2H), 2.10 (s, 3H), 2.04 (s, 3H), 1.78 (t, J=7.6, 3H), 1.47 (s, 3H), 1.39 (s, 3H).

Step E: Preparation of (1S)-3-[(2S,3R)-2-(4-{2-[5-(acetyloxy)-2,2-dimethyl-1,3-dioxan-5-yl] ethyl}phenyl)-1-(4-{3-[(methylsulfonyl)amino] propyl}phenyl)-4-oxoazetidin-3-yl]-1-(4-fluorophenyl)propyl acetate

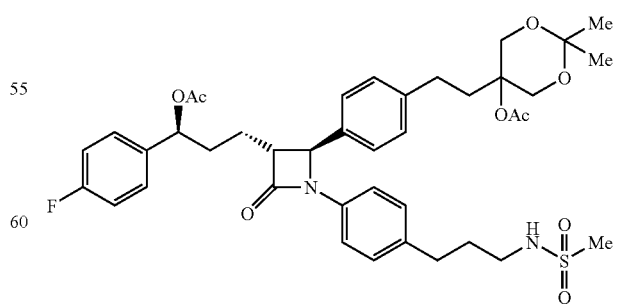

A roundbottom flask was charged with 10% Pd-C (500 mg) and 300 mg 20% Pd(OH)$_2$—C. EtOAc (~2 mL) was added to cover the solid catalyst mixture. To this mixture was added a solution of the intermediate from Step D, (1.5 g, 2.0 mmol) in ethanol (40 mL) and ethyl acetate (2 mL). The resulting suspension set under hydrogen atmosphere and stirred vigorously for 1 hr. The catalysts were filtered, solids washed with ethanol and the solvent was removed under vacuum to obtain partially hydrogenated intermediate. The reaction procedure was repeated as above. A roundbottom flask was charged with 10% Pd-C (500 mg) and 300 mg 20% Pd(OH)$_2$—C. EtOAc (~2 mL) was added to cover the solid catalyst mixture. To this mixture was added a solution of the intermediate from above in ethanol (40 mL) and ethyl acetate (2 mL). The resulting suspension set under hydrogen atmosphere and stirred vigorously for 2 hours. The catalyst was filtered through filter aid and MgSO$_4$ and washed with EtOH/EtOAc. The filtrate was concentrated in vacuo to afford the title compound which was used without further purification. m/z (ES) 692 (M-OAc)$^+$. $^1$HNMR (500 MHz, CD$_3$OD) δ: 7.31-7.24 (m, 6H), 7.21-7.17 (m, 3H), 7.08-7.02 (m, 3H), 5.72 (app t, 6.7 Hz, 1H) 4.60 (d, J=2.1 Hz, 1H), 4.20 (app t, J=6.5, 1H), 4.02 (d, J=12.4 Hz, 2H), 3.90 (d, J=12.2 Hz, 2H), 3.13 (q, J=6.7 Hz, 2H), 3.06 (dt, J=2.2, 7.6 Hz, 1H), 2.94 (s, 3H), 2.60 (app q, 7.4 Hz, 4H), 2.35-2.29 (m, 2H), 2.08 (s, 3H), 2.03 (s, 3H), 1.83-1.90 (m, 3H), 1.45 (s, 3H), 1.40 (s, 3H).

Step F: Preparation of 3-{4-[(2S,3R)-3-[(3S)-3-(acetyloxy)-3-(4-fluorophenyl)propyl]-1(4-{3-[(methylmethylsulfonyl)amino]propyl}phenyl)-4-oxoazetidin-2-yl]phenyl}-1,1-bis(hydroxymethyl)propyl acetate

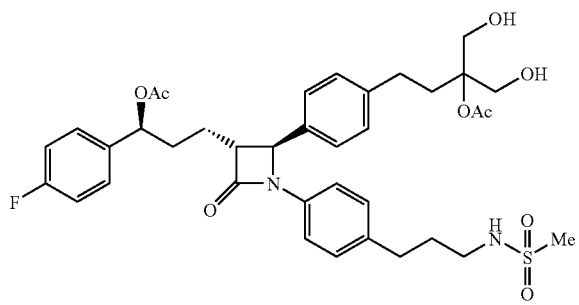

To a solution of the intermediate of step E (1.5 g, 2 mmol) in THF/water (16 mL/4 mL) was added TFA (1 mL). The reaction mixture was stirred at RT for 16 hr. To the reaction mixture was added 100 mL toluene and the water was removed under vacuum with water bath temperature of 40° C. The residue was treated twice with 100 mL toluene followed by azeotropic removal of water. The solvent was completely removed under vacuum. The crude product was purified by MPLC (silica column) with stepwise gradient elution (50-100% EtOAc/hexanes as eluent). Mixed fractions were also isolated and were further purified by prep TLC eluting with CH$_2$Cl$_2$/MeOH (95/5). The purified fractions were combined to afford the title compound. m/z (ES) 653 (M-OAc)$^+$.

Step G: Preparation of N-[3-(4-{(2S,3R)-2-{4-[3,4-dihydroxy-3-(hydroxymethyl)butyl]phenyl}-3-[(3S)-3-(4-fluorophenyl)-3-hydroxypropyl]-4-oxoazetidin-1-yl}phenyl)propyl]methanesulfonamide

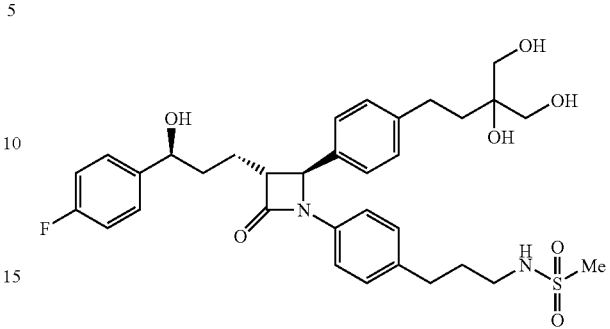

To a solution of the intermediate from Step F, (1.05 g, 1.47 mmol) in methanol (2.5 mL) was added potassium cyanide (100 mg, 1.58 mmol) and the resulting solution stirred at 50° C. for 2 hours. The solution was concentrated and the residue purified by preparative TLC plate eluting with methanol/dichloromethane (10/90) to afford the title compound. This product was further purified by MPLC (silica column) with stepwise gradient elution; (5-10% EtOH/EtOAc as eluent) to afford the title compound as a white solid. m/z (ES) 611 (M-OAc)$^+$ and 651 (M+Na)$^+$ $^1$HNMR (500 MHz, CD$_3$OD) δ: 7.35-7.31 (m, 2H), 7.28-7.234 (m, 4H), 7.18 (d, J=8.5 Hz, 2H), 7.10 (d, J=8.6 Hz, 2H), 7.03 (app, t, J=8.6 Hz, 2H), 4.79 (br d, J=2.1 Hz, 1H), 4.60 (br dd, J=5.1, 6.60 Hz, 1H), 3.53 (s, 4H)), 3.09-3.03 (m, 1H), 3.02 (t, J=6.8 Hz, 2H), 2.88 (s, 3H), 2.73-2.67 (m, 2H), 2.61 (t, 7.6 Hz, 2H), 1.97-1.83 (m, 3H), 1.81-1.73 (m, 3H).

EXAMPLE 2

N-[3-(4-{(2S,3R)-3-[(3S)-3-(4-fluorophenyl)-3-hydroxypropyl]-2-[4-(6-hydroxyhexyl)phenyl]-4-oxoazetidin-1-yl}phenyl)propyl]-N-methylmethanesulfonamide (compound of Table 1 wherein x is 4, y is 1 and R$^{10}$ is Me)

Step A: Preparation of 4-[(2S,3R)-3-[(3S)-3-(acetyloxy)-3-(4-fluorophenyl)propyl]-1-(4-{3-[methyl(methylsulfonyl)amino]prop-1-yn-1-yl}phenyl)-4-oxoazetidin-2-yl]phenyl acetate (i-9 wherein R$^{10}$ is —CH$_3$)

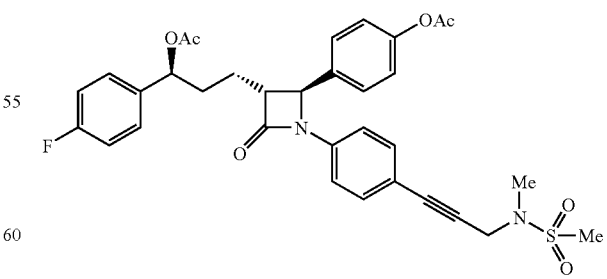

Dichlorobis(triphenylphosphine)palladium(II) (35 mg, 0.050 mmol) and copper(I) iodide (19 mg, 0.10 mmol) were added to a solution of i-8 (0.15 g, 0.25 mmol) and i-2 (44 mg, 0.30 mmol) in triethylamine (0.17 mL, 1.2 mmol) and DMF (1.3 mL). The reaction mixture was saturated with nitrogen and stirred at room temperature. After 14 h, the reaction mixture was quenched with saturated aqueous ammonium chloride and extracted three times with EtOAc. The combined organic extracts were washed with water, brine, dried (Na$_2$SO$_4$) and concentrated in vacuo. Purification of the crude residue by flash chromatography on silica gel (gradient elution; 20%-35% EtOAc/hexanes as eluent) afforded the title compound m/z (ES) 561 (M-OAc)$^+$. $^1$HNMR (500 MHz, CDCl$_3$) δ: 7.35 (d, J=8.5 Hz, 1H), 7.28 (dd, J=6.4, 8.4 Hz, 1H), 7.19 (d, J=8.1 Hz, 1H), 7.12 (d, J=8.5 Hz, 1H), 7.08 (d, J=8.2 Hz, 1H), 7.02 (dd, J=6.5, 8.6 Hz, 1H), 5.72 (t, 6.6 Hz, 1H), 4.62 (d, J=2.3 Hz, 1H), 4.15 (dd, J=7.1, 11 Hz, 1H), 3.15-3.12 (m, 2H), 3.08-3.05 (m, 1H), 2.84 (s, 3H), 2.78 (s, 3H), 2.60 (t, 7.4 Hz, 2H), 2.32 (s, 3H), 2.07 (overlapped s, 3H), 2.09-2.03 (m, 2H), 1.90-1.83 (m, 4H).

Step B: Preparation of 4-[(2S,3R)-3-[(3S)-3-(acetyloxy)-3-(4-fluorophenyl)propyl]-1-(4-{3-[methyl(methylsulfonyl)amino]propyl}phenyl)-4-oxoazetidin-2-yl]phenyl acetate (i-10a wherein R$^{10}$ is CH$_3$)

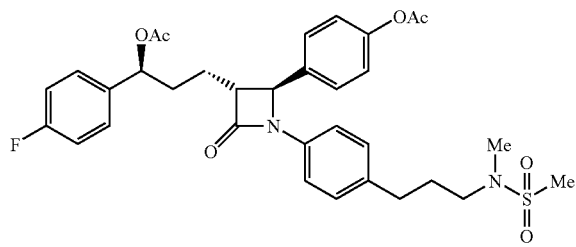

A mixture of the intermediate from Step A (805 mg, 1.30 mmol) and palladium hydroxide (150 mg of 20 wt. % on activated carbon) in EtOAc (25 mL) was hydrogenated at atmospheric pressure. After 8 h, the reaction mixture was filtered through a short column of filter aid eluting copiously with EtOAc. The filtrate was concentrated in vacuo to afford the title compound. m/z (ES) 565 (M-OAc)$^+$. $^1$HNMR (500 MHz, CDCl$_3$) δ: 7.35 (d, J=8.5 Hz, 1H), 7.28 (dd, J=5.4, 8.4 Hz, 1H), 7.28-7.20 (m, 1H), 7.14 (d, J=6.6 Hz, 1H), 7.06 (d, J=8.5 Hz, 1H), 7.04 (dd, J=6.5, 8.6 Hz, 1H), 5.72 (t, 7.1 Hz, 1H), 4.64 (d, J=2.5 Hz, 1H), 4.28 (s, 2H), 3.10 (dt, J=2.4, 7.6 Hz, 1H), 2.99 (s, 3H), 2.94 (s, 3H), 2.33 (s, 3H), 2.08 (overlapped s, 3H), 2.09-2.03 (m, 2H), 1.90-1.83 (m, 4H).

Step C: Preparation of (1S)-1-(4-fluorophenyl)-3-[(3R,4S)-1-(4-{3-[methyl(methylsulfonyl)-amino]propyl}phenyl)-2-oxo-4-(4-{[(trifluoromethyl)sulfonyl]oxy}phenyl)azetidin-3-yl]propyl acetate (i-10b wherein R$^{10}$=CH$_3$)

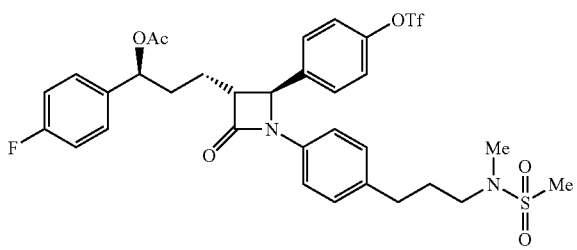

Guanidine (13 mg, 0.13 mmol) was added to a mixture of the intermediate from Step B (82 mg, 0.13 mmol) and triethylamine (18 µL, 0.13 mmol) in methanol (2 mL). After 3 h, the reaction mixture was quenched with saturated aqueous ammonium chloride and extracted three times with EtOAc. The combined organic extracts were washed with water, brine, dried (Na$_2$SO$_4$) and concentrated in vacuo to afford a clear oil which was dissolved in CH$_2$Cl$_2$ (1.5 mL). Triethylamine (24 mL, 0.17 mmol), DMAP (2.0 mg, 0.016 mmol) and (bis(trifluoromethylsulfonyl)amino)pyridine (77 mg, 0.13 mmol) were added successively to the above solution. After 3 h, the reaction was quenched with 0.5N aq. HCl and extracted three times with EtOAc. The combined organic extracts were washed with water, brine, dried (Na$_2$SO$_4$) and concentrated in vacuo. Purification of the crude residue by flash chromatography on silica gel (gradient elution; 35%-40% EtOAc/hexanes as eluent) afforded the title compound. m/z (ES) 655 (M-OAc)$^+$. $^1$HNMR (500 MHz, CDCl$_3$) δ: 7.43 (d, J=8.6 Hz, 1H), 7.32-7.28 (m, 2H), 7.15 (d, J=6.4 Hz, 1H), 7.10 (d, J=8.4 Hz, 1H), 7.04 (t, J=6.5 Hz, 1H), 5.72 (t, 6.6 Hz, 1H), 4.66 (d, J=2.3 Hz, 1H), 3.14 (dt, J=2.6, 6.6 Hz, 2H), 3.08 (dt, J=2.5, 8.2 Hz, 1H), 2.84 (s, 3H), 2.79 (s, 3H), 2.61 (t, 7.7 Hz, 2H), 2.08 (overlapped s, 3H), 2.09-2.04 (m, 2H), 1.93-1.84 (m, 4H).

Step D: Preparation of (1S)-3-[(2S,3R)-2-{4-[6-(benzyloxy)hex-1-yn-1-yl]phenyl}-1-(4-{3-[methyl(methylsulfonyl)amino]propyl}phenyl)-4-oxoazetidin-3-yl]-1-(4-fluorophenyl)propyl acetate

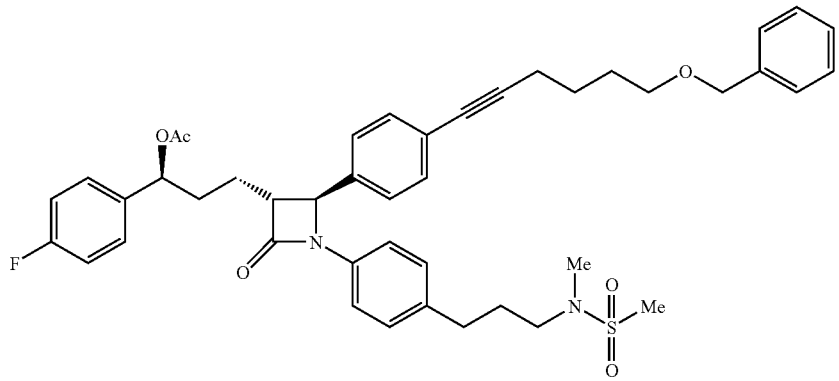

The title compound was prepared from intermediate step C and benzyl hex-5-yn-1-yl ether (i-11) according to the procedure of Example 1, step D. The crude product was purified by preparative TLC plate eluting with ethyl acetate/hexanes (65/35) to afford the title compound. m/z (ES) 693 (M-OAc)+.

Step E: Preparation of (1S)-3-[(2S,3R)-2-{4-[6-(benzyloxy)hexyl[phenyl}-1-(4-{3-[methyl(methylsulfonyl)amino]propyl}phenyl)-4-oxoazetidin-3-yl]-1-(4-fluorophenyl)propyl acetate

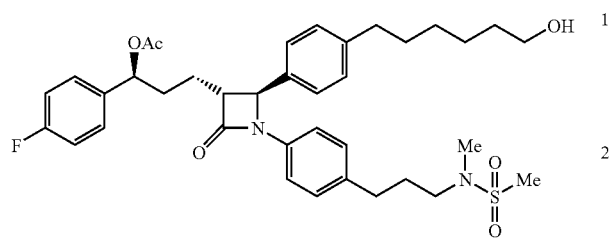

The title compound was prepared from the intermediate of step D according to the procedure for Example 1, step B. The crude product was purified by preparative TLC plates eluting with EtOAc/hexanes (80/20) to afford the title compound m/z (ES) 607 (M-OAc)+.

Step F: Preparation of N-[3-(4-{(2S,3R)-3-[(3S)-3-(4-fluorophenyl)-3-hydroxypropyl]-2-[4-(6-hydroxyhexyl)phenyl]-4-oxoazetidin-1-yl}phenyl)propyl]-N-methylmethanesulfonamide

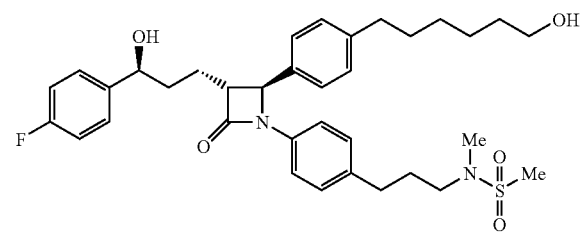

The title compound was prepared from the intermediate of Step E according to the procedure for Example 1, step F. The crude product was purified by preparative TLC plate eluting with EtOAc/hexanes (90/10) to afford the title compound. m/z (ES) 607 (M-OAc)+, 625 (M+H)+ and 647 (M+Na)+.
¹HNMR (500 MHz, CD₃OD) δ: 7.35-7.30 (m, 2H), 7.27 (d, J=8.1 Hz, 2H), 7.22-7.15 (m, 2H), 7.10 (d, J=8.4 Hz, 2H), 7.05-7.00 (m, 2H), 4.78 (d, J=1.8 Hz, 1H), 4.60 (br t, J=6.8 Hz, 1H), 3.52 (t, J=6.6 Hz, 2H), 3.08-3.02 (m, 1H), 3.02 (t, J=6.9 Hz, 2H), 2.95 (s, 3H), 2.89 (s, 3H), 2.65-2.58 (m, 4H), 1.98-1.84 (m, 4H), 1.78 (p, J=7 Hz, 2H), 1.62 (app. p, J=7.1 Hz, 2H), 1.55-1.47 (m, 2H), 1.40-1.32 (m, 2H).

EXAMPLE 3

N-[3-(4-{(2S,3R)-2-{4-[3,4-dihydroxy-3-(hydroxymethyl)butyl]-2-hydroxyphenyl}-3-[(3S)-3-(4-fluorophenyl)-3-hydroxypropyl]-4-oxoazetidin-1-yl}phenyl)propyl)methanesulfonamide (compound of Table 3 wherein y is 1, R¹³ is OH and R¹⁰ is H)

Step A: Preparation of (1S)-3-[(2S,3R)-2-[2,4-bis(benzyloxy)phenyl]-1-(4-{3-[(methylsulfonyl)amino]prop-1-yn-1-yl}phenyl)-4-oxoazetidin-3-yl]-1-(4-fluorophenyl)propyl acetate

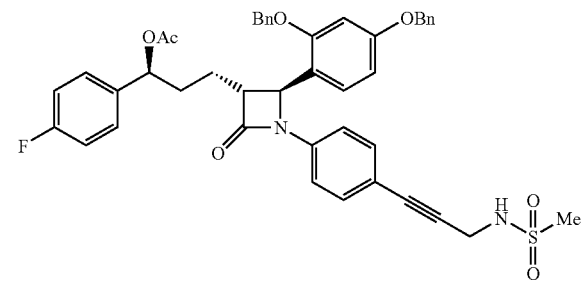

The title compound was prepared from i-12 and i-1 according to the procedure for Example 1, step A. m/z (ES) 701 (M-OAc)+.

Step B: Preparation of (1S)-3-[(2S,3R)-2-[2-(benzyloxy)-4-hydroxyphenyl]-1-(4-{3-[(methylsulfonyl)amino]propyl}phenyl)-4-oxoazetidin-3-yl]-1-(4-fluorophenyl)propyl acetate

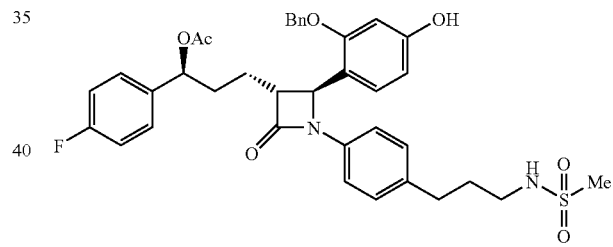

The title compound was prepared from the intermediate from Step A according to the procedure for Example 1, step B and used without further purification. m/z (ES) 615 (M-OAc)+.

Step C: Preparation of (1S)-3-[(2S,3R)-2-(2-(benzyloxy)-4-{[(trifluoromethyl)sulfonyl]-oxy}phenyl)-1-(4-{3-[(methylsulfonyl)amino]propyl}phenyl)-4-oxoazetidin-3-yl]-1-(4-fluorophenyl)propyl acetate

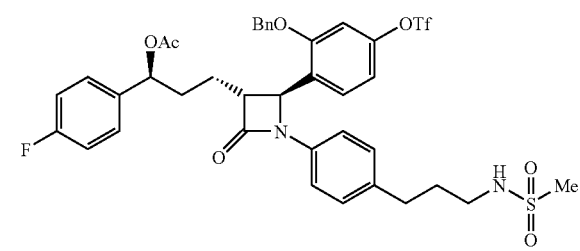

To a solution of 110 mg (0.163 mmol) of the intermediate of step B in methylene chloride (4 mL) under nitrogen atmosphere at 0° C. was added simultaneously by syringe, pyridine (0.015 mL, 0.18 mmol) and triflic anhydride (0.031 mL, 0.18 mmol). The resulting solution was stirred for 2 h at ambient temperature. The reaction mixture was concentrated in vacuo and the residue was purified by 15 prep TLC (EtOAc/hexanes as eluent) to afford the title compound. m/z (ES) 807 (M+H)$^+$, 747 (M-OAc)$^+$.

Step D: Preparation of (1S)-3-[(2S,3R)-2-[4-{[5-(acetyloxy)-2,2-dimethyl-1,3-dioxan-5-yl]ethynyl}-2-(benzyloxy)phenyl]-1-(4-{3-[(methylsulfonyl)amino]propyl}phenyl)-4-oxoazetidin-3-yl]-1-(4-fluorophenyl)propyl acetate

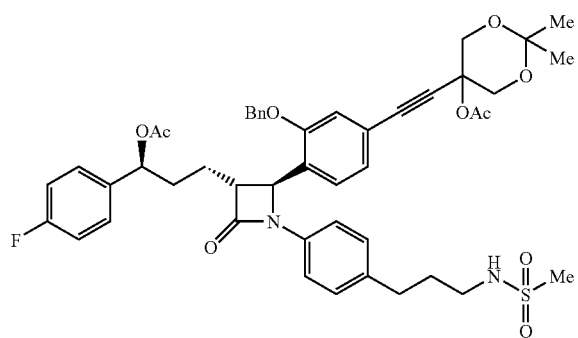

The title compound was prepared from the intermediate of step C and 5-ethynyl-2,2-dimethyl-1,3-dioxan-5-yl acetate (i-6) according to the procedure for Example 1, step D. Purification of the crude product by prep TLC (EtOAc/hexanes as eluent) gave the title compound. m/z (ES) 795 (M-OAc)$^+$.

Step E: Preparation of 3-[4-[(2S,3R)-3-[(3S)-3-(acetyloxy)-3-(4-fluorophenyl)propyl]-1-(4-{3-[(methylsulfonyl)amino]propyl}phenyl)-4-oxoazetidin-2-yl]-3-(benzyloxy)phenyl]-1,1-bis(hydroxymethyl)prop-2-yn-1-yl acetate

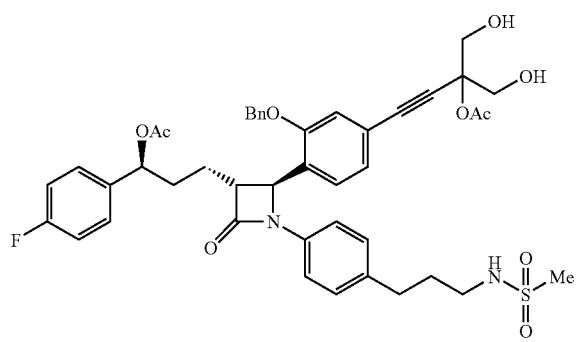

The title compound was prepared from the intermediate of step D, according to the procedure for Example 1, step F. m/z (ES) 755 (M-OAc)$^+$.

Step F: Preparation of N-[3-(4-{(2S,3R)-2-{2-(benzyloxy)-4-[3,4-dihydroxy-3-(hydroxymethyl)but-1-yn-1-yl]phenyl}-3-[(3 S)-3-(4-fluorophenyl)-3-hydroxypropyl]-4-oxoazetidin-1-yl}phenyl)propyl] methanesulfonamide

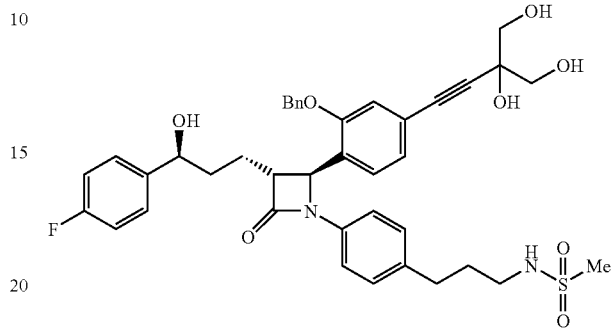

The title compound was prepared from the intermediate of step E according to the procedure for Example 1, step G. m/z (ES) 753 (M+Na)$^+$, 714 (M-OH)$^+$.

Step G: Preparation of N-[3-(4-{(2S,3R)-2-{4-[3,4-dihydroxy-3-(hydroxymethyl)butyl]-2-hydroxyphenyl}-3-[(3S)-3-(4-fluorophenyl)-3-hydroxypropyl]-4-oxoazetidin-1-yl}phenyl)propyl] methanesulfonamide

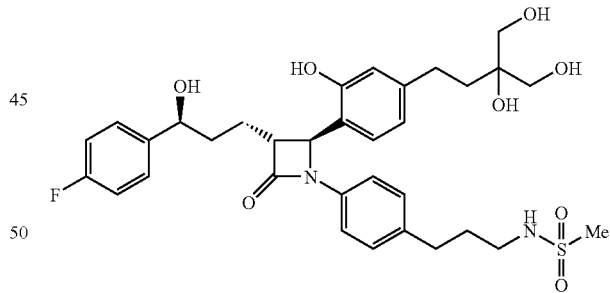

The title compound was prepared from the intermediate of step F according to the procedure for Example 1, step E. m/z (ES) 667 (M+Na)$^+$, 645 (M+H)$^+$, 627 (M−OH)$^+$. $^1$HNMR (500 MHz, CD$_3$OD) δ: 7.50 (d, J=8.5 HZ, 1H), 7.34-7.30 (m, 1H), 7.22-7.18 (m, 4H), 7.18-7.10 (m, 2H), 7.05-6.98 (m, 2H), 4.68 (br d, J=2.3 Hz, 1H), 4.59 (app. t, J=6.7 Hz, 1H), 3.53 (s, 4H), 3.10-3.02 (m, 1H), 3.02 (t, J=6.9 Hz, 2H), 2.90 (s, 3H), 2.74-2.66 (m, 2H), 2.60 (t, J=7.5 Hz, 2H), 1.97-1.84 (m, 3H), 1.82-1.73 (m, 3H).

Employing procedures similar to those described in Examples 1-3, the following compounds in Table 1 were prepared from the appropriate starting materials:

TABLE 1

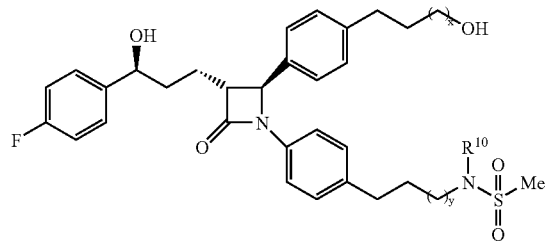

| Example # | x | y | R$^{10}$ | m/z (ES) |
|---|---|---|---|---|
| 4 | 3 | 1 | Me | 633 (M + Na)$^+$, 593 (M − OH)$^+$ |
| 5 | 4 | 1 | H | 611 (M + H)$^+$, 593 (M − OH)$^+$ |
| 6 | 1 | 1 | H | 569 (M + H)$^+$, 551 (M − OH)$^+$ |
| 7 | 2 | 1 | H | 565 (M − H)$^+$ |
| 8 | 3 | 4 | H | 621 (MH − H$_2$O)$^+$ |
| 9 | 4 | 4 | H | 635 (MH − H$_2$O)$^+$ |
| 10 | 1 | 4 | H | 593 (MH − H$_2$O)$^+$ |
| 11 | 2 | 4 | H | 607 (MH − H$_2$O)$^+$ |
| 12 | 2 | 2 | H | 579 (MH − H$_2$O)$^+$ |
| 13 | 3 | 2 | H | 593 (MH − H$_2$O)$^+$ |
| 14 | 4 | 2 | H | 607 (MH − H$_2$O)$^+$ |
| 15 | 2 | 3 | H | 593 (MH − H$_2$O)$^+$ |
| 16 | 3 | 3 | H | 607 (MH − H$_2$O)$^+$ |
| 17 | 4 | 3 | H | 621 (MH − H$_2$O)$^+$ |
| 18 | 1 | 2 | H | 565 (MH − H$_2$O)$^+$ |
| 19 | 1 | 3 | H | 579 (MH − H$_2$O)$^+$ |

Employing procedures similar to those described in Examples 1-3, the following pounds in Table 2 were prepared from the appropriate starting materials:

TABLE 2

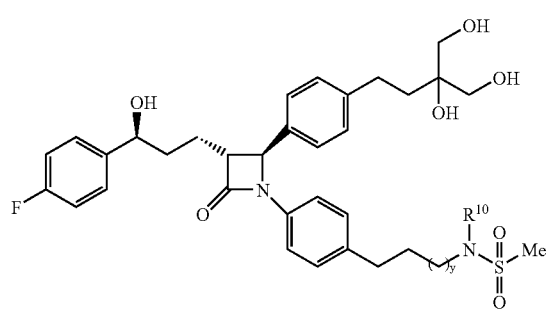

| Example # | y | R$^{10}$ | m/z (ES) |
|---|---|---|---|
| 20 | 2 | H | 625 (MH − H$_2$O)$^+$ |
| 21 | 3 | H | 639 (MH − H$_2$O)$^+$ |
| 22 | 4 | H | 653 (MH − H$_2$O)$^+$ |

Employing procedures similar to those described in Examples 1-3, the following compounds in Table 3 may be prepared from the appropriate starting materials:

TABLE 3

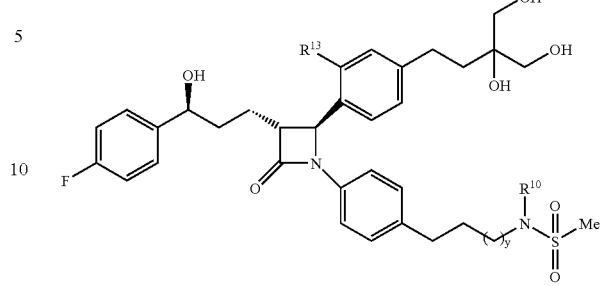

| Example # | y | R$^{13}$ | R$^{10}$ |
|---|---|---|---|
| 23 | 2 | OH | H |
| 24 | 3 | OH | H |
| 25 | 4 | OH | H |
| 26 | 2 | OH | Me |
| 27 | 3 | OH | Me |
| 28 | 4 | OH | Me |

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agents used in the instant invention as indicated above. Likewise, the specific pharmacological responses observed may vary according to and depending upon the particular active compound selected or whether there are present pharmaceutical carriers, as well as the type of formulation employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural Formula I

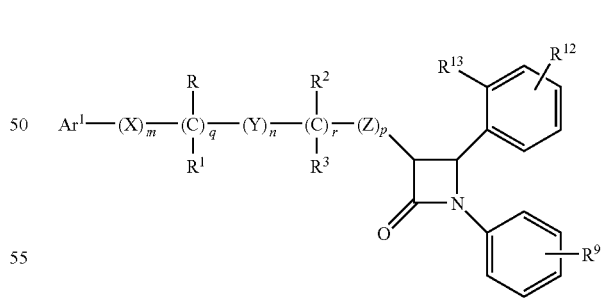

I and the pharmaceutically acceptable salts and esters thereof, wherein

Ar$^1$ is selected from the group consisting of aryl and R$^4$-substituted aryl;

X, Y and Z are independently selected from the group consisting of —CH$_2$—, —CH(C$_{1-6}$alkyl)— and —C(C$_{1-6}$alkyl)$_2$—;

R is selected from the group consisting of —OR$^6$, —O(CO)R$^6$, —O(CO)O R$^8$, and —O(CO)NR$^6$R$^7$;

R¹ is selected from the group consisting of —H, —$C_{1-6}$ alkyl and aryl, or R and R¹ together are oxo;

R² is selected from the group consisting of —OR⁶, —O(CO)R⁶, —O(CO)OR⁸ and —O(CO)NR⁶R⁷;

R³ is selected from the group consisting of —H, —$C_{1-6}$ alkyl and aryl, or R² and R³ together are oxo;

q and r are integers each independently selected from 0 and 1 provided that at least one of q and r is 1;

m, n and p are integers each independently selected from 0, 1, 2, 3 and 4; provided that the sum of m, n, p, q and r is 1, 2, 3, 4, 5 or 6; and provided that when p is 0 and r is 1, then the sum of m, q and n is 1, 2, 3, 4, or 5;

t is an integer selected from 0, 1 and 2;

R⁴ is 1-5 substituents independently selected at each occurrence from the group consisting of:
—OR⁵, —O(CO)R⁵, —O(CO)OR⁸, —O—$C_{1-5}$alkyl-OR⁵, —O(CO)NR⁵R⁶, —NR⁵R⁶, —NR⁵(CO)R⁶, —NR⁵(CO)OR⁸, —NR⁵(CO)NR⁶R⁷, —NR⁵SO₂R⁸, —COOR⁵, —CONR⁵R⁶, —COR⁵, —SO₂NR⁵R⁶, —S(O)$_t$R⁸, —O—$C_{1-10}$alkyl-COOR⁵, —O—$C_{1-10}$alkyl-CONR⁵R⁶ and fluoro;

R⁵, R⁶ and R⁷ are independently selected at each occurrence from the group consisting of —H, —$C_{1-6}$alkyl, aryl and aryl-substituted —$C_{1-6}$alkyl;

R⁸ is selected from the group consisting of —$C_{1-6}$alkyl, aryl and aryl-substituted —$C_{1-6}$alkyl;

R⁹ is selected from the group consisting of —C≡C—$(CH_2)_y$-NR¹⁰R¹¹, —C=C—$(CH_2)y$-NR¹⁰R¹¹ and —$(CH_2)_w$-NR¹⁰R¹¹;

w is an integer selected from 1, 2, 3, 4, 5, 6, 7 and 8; and y is an integer selected from 1, 2, 3, 4, 5 and 6; and R¹⁰ is selected from the group consisting of —H and —$C_{1-3}$ alkyl;

R¹¹ is selected from the group consisting of —H, —$C_{1-3}$ alkyl, —C(O)—$C_{1-3}$alkyl, —C(O)—NR¹⁰R¹⁰, —SO₂—$C_{1-3}$alkyl, and —SO₂-phenyl;

R¹² is selected from the group consisting of —$C_{1-15}$alkyl mono- or poly-substituted with —OH, —CH=CH—$C_{1-13}$alkyl mono- or poly-substituted with —OH, —C≡C—$C_{1-13}$alkyl mono- or poly-substituted with —OH, and

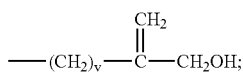

v is an integer selected from 0 and 1; and

R¹³ is selected from the group consisting of —H and —OH.

2. The compound of claim 1 wherein r is zero and m is zero.

3. The compound of claim 2 wherein Ar¹ is selected from the group consisting of aryl and R⁴-substituted aryl wherein R⁴ is 1-2 substituents independently selected at each occurrence from the group consisting of: —OR⁵, —O(CO)R⁵, —O(CO)OR⁸, —O—$C_{1-5}$alkyl-OR⁵, —O(CO)NR⁵R⁶, —NR⁵R⁶, —NR⁵(CO)R⁶, —NR⁵(CO)OR⁸, —NR⁵(CO)NR⁶R⁷, —NR⁵SO₂R⁸, —COOR⁵, —CONR⁵R⁶, —COR⁵, —SO₂NR⁵R⁶, —S(O)$_t$R⁸, —O—$C_{1-10}$alkyl -COOR⁵, —O—$C_{1-10}$alkyl-CONR⁵R⁶ and fluoro.

4. The compound of claim 3 wherein R is —OR⁶ and R¹ is —H.

5. The compound of claim 1 having structural Formula Ia

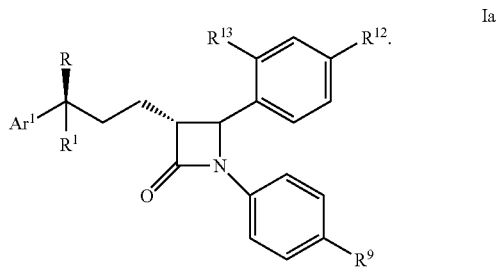

6. The compound of claim 5 wherein Ar¹ is selected from the group consisting of phenyl and R⁴-substituted phenyl wherein R⁴ is 1-2 substituents independently selected at each occurrence from the group consisting of:
—OR⁵, —O(CO)R⁵, —O(CO)OR⁸, —O—$C_{1-5}$alkyl-OR⁵, —O(CO)NR⁵R⁶, —NR⁵R⁶, —NR⁵(CO)R⁶, —NR⁵(CO)OR⁸, —NR⁵(CO)NR⁶R⁷, —NR⁵SO₂R⁸, —COOR⁵, —CONR⁵R⁶, —COR⁵, —SO₂NR⁵R⁶, —S(O)$_t$R⁸, —O—$C_{1-10}$alkyl-COOR⁵, —O—$C_{1-10}$alkyl-CONR⁵R⁶ and fluoro.

7. The compound of claim 6 wherein R is —OR⁶ and R¹ is —H.

8. The compound of claim 7 wherein R⁹ is —$(CH_2)_w$-NR¹⁰R¹¹.

9. The compound of claim 1 having structural Formula Ib

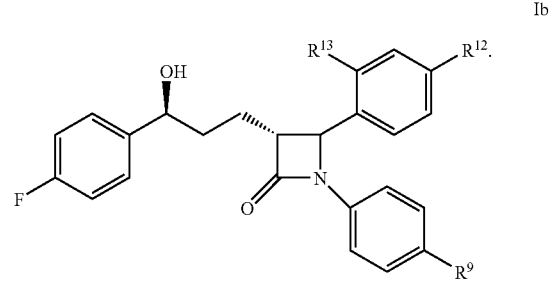

10. The compound of claim 9 wherein R⁹ is —$(CH_2)_w$-NR¹⁰R¹¹.

11. The compound of claim 1 selected from the group consisting of:

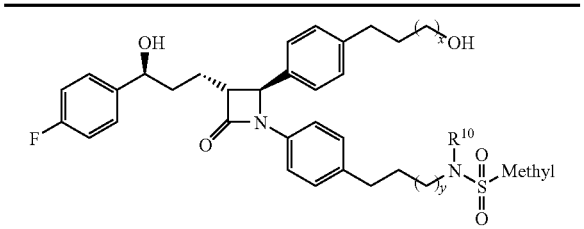

| Example # | x | y | R¹⁰ |
|---|---|---|---|
| 2 | 4 | 1 | Methyl; |
| 4 | 3 | 1 | Methyl; |
| 5 | 4 | 1 | H; |
| 6 | 1 | 1 | H; |
| 7 | 2 | 1 | H; |
| 8 | 3 | 4 | H; |

-continued

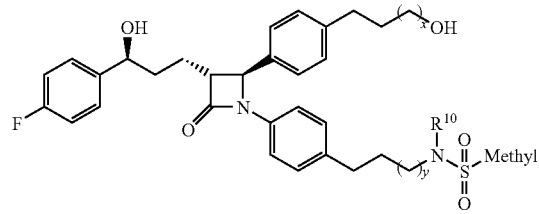

| Example # | x | y | R¹⁰ |
|---|---|---|---|
| 9 | 4 | 4 | H; |
| 10 | 1 | 4 | H; |
| 11 | 2 | 4 | H; |
| 12 | 2 | 2 | H; |
| 13 | 3 | 2 | H; |
| 14 | 4 | 2 | H; |
| 15 | 2 | 3 | H; |
| 16 | 3 | 3 | H; |
| 17 | 4 | 3 | H; |
| 18 | 1 | 2 | H; |
| 19 | 1 | 3 | H; | and the pharmaceutically acceptable salts and esters thereof.

12. The compound of claim 1 selected from the group consisting of:

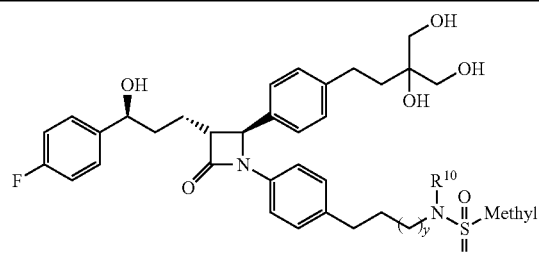

| Example # | y | R¹⁰ |
|---|---|---|
| 1 | 1 | H; |
| 20 | 2 | H; |
| 21 | 3 | H; |
| 22 | 4 | H; | and the pharmaceutically acceptable salts and esters thereof.

13. The compound of claim 1 selected from the group consisting of:

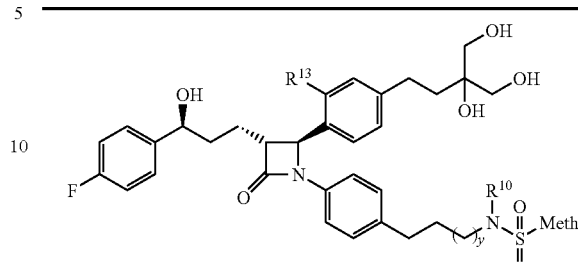

| Example # | y | R¹³ | R¹⁰ |
|---|---|---|---|
| 3 | 1 | OH | H; |
| 23 | 2 | OH | H; |
| 24 | 3 | OH | H; |
| 25 | 4 | OH | H; |
| 26 | 2 | OH | Methyl; |
| 27 | 3 | OH | Methyl; |
| 28 | 4 | OH | Methyl; | and the pharmaceutically acceptable salts and esters thereof.

14. A method of reducing plasma LDL-cholesterol levels comprising administering a therapeutically effective amount of a compound of claim 1 to a patient in need of such treatment.

15. The method of claim 14 comprising administering a therapeutically effective amount of a compound of claim 1 in combination with a therapeutically effective amount of a cholesterol biosynthesis inhibitor to a patient in need of such treatment.

16. A method of treating hypercholesterolemia comprising administering a therapeutically effective amount of a compound of claim 1 to a patient in need of such treatment.

17. A method of treating or reducing the risk for developing atherosclerosis comprising administering a therapeutically effective amount of a compound of claim 1 to a patient in need of such treatment.

18. A method of reducing the risk for having an atherosclerotic disease event comprising administering a prophylactically effective amount of a compound of claim 1 to a patient in at risk for such an event.

19. A pharmaceutical composition comprising a compound of claim 1 and a pharmaceutically acceptable carrier.

20. The pharmaceutical composition of claim 19 additionally comprising a cholesterol biosynthesis inhibitor.

* * * * *